US011517534B2

(12) United States Patent
Oliveira Varum et al.

(10) Patent No.: US 11,517,534 B2
(45) Date of Patent: *Dec. 6, 2022

(54) DELAYED RELEASE DRUG FORMULATION

(71) Applicant: Tillotts Pharma AG, Rheinfelden (CH)

(72) Inventors: Felipe Josè Oliveira Varum, Basel (CH); Roberto Carlos Bravo González, Binningen (CH); Thomas Buser, Nuglar (CH); Abdul Waseh Basit, Harrow (GB); Ana Cristina Freire, Northampton (GB)

(73) Assignee: Tillotts Pharma AG, Rheinfelden (CH)

( * ) Notice: Subject to any disclaimer, the term of this patent is extended or adjusted under 35 U.S.C. 154(b) by 0 days.

This patent is subject to a terminal disclaimer.

(21) Appl. No.: 15/612,065

(22) Filed: Jun. 2, 2017

(65) Prior Publication Data

US 2017/0266117 A1    Sep. 21, 2017

Related U.S. Application Data

(63) Continuation of application No. 14/066,054, filed on Oct. 29, 2013, now Pat. No. 9,814,681, which is a continuation-in-part of application No. PCT/EP2013/058921, filed on Apr. 29, 2013, which is a continuation-in-part of application No. PCT/EP2013/058923, filed on Apr. 29, 2013.

(60) Provisional application No. 61/640,217, filed on Apr. 30, 2012, provisional application No. 61/640,217, filed on Apr. 30, 2012.

(30) Foreign Application Priority Data

Apr. 30, 2012 (EP) .................................... 12166110

(51) Int. Cl.
*A61K 9/28* (2006.01)
*A61K 31/196* (2006.01)
*A61K 31/606* (2006.01)
*A61K 31/616* (2006.01)
*A61K 47/32* (2006.01)
*A61K 47/36* (2006.01)
*A61K 47/38* (2006.01)
*A61K 9/00* (2006.01)
*A61K 9/20* (2006.01)

(52) U.S. Cl.
CPC .......... *A61K 9/2886* (2013.01); *A61K 9/0053* (2013.01); *A61K 9/2013* (2013.01); *A61K 9/2054* (2013.01); *A61K 9/284* (2013.01); *A61K 9/286* (2013.01); *A61K 9/288* (2013.01); *A61K 9/2846* (2013.01); *A61K 9/2866* (2013.01); *A61K 9/2893* (2013.01); *A61K 31/196* (2013.01); *A61K 31/606* (2013.01); *A61K 31/616* (2013.01); *A61K 47/32* (2013.01); *A61K 47/36* (2013.01); *A61K 47/38* (2013.01)

(58) Field of Classification Search
None
See application file for complete search history.

(56) References Cited

U.S. PATENT DOCUMENTS

| 5,171,580 | A | * | 12/1992 | Lamartino | ............. | A61P 29/00 424/490 |
| 5,422,121 | A | * | 6/1995 | Lehmann | ............. | A61K 9/1635 424/464 |
| 5,502,077 | A | | 3/1996 | Breivik et al. | | |
| 5,508,276 | A | | 4/1996 | Anderson et al. | | |
| 5,656,290 | A | | 8/1997 | Kelm et al. | | |
| 5,683,722 | A | | 11/1997 | Derrieu et al. | | |
| 5,914,132 | A | * | 6/1999 | Keim | ..................... | A61K 9/145 424/467 |
| 6,365,185 | B1 | * | 4/2002 | Ritschel | ............... | A61K 9/0004 424/464 |
| 6,391,341 | B1 | * | 5/2002 | Mendes | ............... | A61K 9/5078 424/400 |
| 6,395,185 | B1 | | 5/2002 | Gauthier et al. | | |
| 9,161,918 | B2 | | 10/2015 | Venkatesh | | |

(Continued)

FOREIGN PATENT DOCUMENTS

CN    102 319 218 A    1/2012
DE    102009033621      1/2011

(Continued)

OTHER PUBLICATIONS

"Innovative Drug Delivery Systems for Colon Targeting" 2008.*
"Determination of Surface Free Energies and Aspect Ratio of Talc Chapter 1 Mineralogy of Talc" 2004.*
Dictionary of Archives Terminology SAA alkaline-reserve paper.*
Akatsuka "Buffering Effects of Calcium Carbonate as Clarified by Sevelamer Hydrochloride Monotherapy" abstract 2008.*
International Search Report and Written Opinion dated Jul. 11, 2013 in PCT/EP2013/058921.

(Continued)

Primary Examiner — Danah Al-Awadi
(74) Attorney, Agent, or Firm — Grüneberg and Myers PLLC

(57) ABSTRACT

In a delayed release formulation comprising a core containing a drug and a delayed release coating for providing intestinal release, release of the drug in the colon is accelerated by including an isolation layer between the core and the delayed release coating. The delayed release coating comprises an inner layer and an outer layer. The outer layer comprises a pH dependently soluble polymeric material which has a pH threshold at about pH 5 or above. The inner layer comprises a soluble polymeric material which is soluble in intestinal fluid or gastrointestinal fluid, said soluble polymeric material being selected from the group consisting of a polycarboxylic acid polymer that is at least partially neutralised, and a non-ionic polymer, provided that, where said soluble polymeric material is a non-ionic polymer, said inner layer comprises at least one additive selected from a buffer agent and a base.

31 Claims, 6 Drawing Sheets

(56) References Cited

U.S. PATENT DOCUMENTS

| | | | |
|---|---|---|---|
| 9,161,919 | B2 | 10/2015 | Venkatesh |
| 9,364,440 | B2 | 6/2016 | Bravo Gonzalez et al. |
| 9,566,249 | B2 | 2/2017 | Venkatesh |
| 9,579,293 | B2 | 2/2017 | Venkatesh |
| 9,597,293 | B2 | 3/2017 | Liu et al. |
| 9,814,681 | B2 | 11/2017 | Oliveira Varum et al. |
| 10,226,430 | B2 | 3/2019 | Bravo Gonzalez et al. |
| 10,272,048 | B2 | 4/2019 | Oliveira Varum et al. |
| 10,537,430 | B2 | 1/2020 | Liu et al. |
| 2002/0139461 | A1 | 10/2002 | Pyle et al. |
| 2002/0192282 | A1 | 12/2002 | Beckert et al. |
| 2003/0035839 | A1 | 2/2003 | Hirsh et al. |
| 2003/0139461 | A1 | 7/2003 | Li et al. |
| 2004/0028737 | A1 | 2/2004 | Deshpande et al. |
| 2004/0147605 | A1 | 7/2004 | Onuki et al. |
| 2005/0037439 | A1 | 2/2005 | Bourner et al. |
| 2005/0214372 | A1* | 9/2005 | Di Capua .......... A61K 31/4439 424/472 |
| 2007/0243253 | A1* | 10/2007 | Basit .......... A61P 31/00 424/471 |
| 2008/0193531 | A1 | 8/2008 | Hermelin et al. |
| 2008/0200482 | A1 | 8/2008 | Petereit et al. |
| 2009/0162434 | A1 | 6/2009 | Ugwoke et al. |
| 2009/0175935 | A1 | 7/2009 | Setty et al. |
| 2010/0129446 | A1 | 5/2010 | Liu et al. |
| 2010/0179170 | A1* | 7/2010 | Du Toit .......... A61K 31/495 514/254.11 |
| 2010/0209520 | A1* | 8/2010 | Kubo .......... A61K 9/5078 514/1.1 |
| 2010/0285123 | A1 | 11/2010 | Prasad et al. |
| 2011/0034555 | A1 | 2/2011 | Osterloh et al. |
| 2011/0097394 | A1 | 4/2011 | Sachetto et al. |
| 2011/0177164 | A1 | 7/2011 | Rajan et al. |
| 2011/0217374 | A1 | 9/2011 | Oh et al. |
| 2011/0274753 | A1 | 11/2011 | Cifter et al. |
| 2013/0058986 | A1 | 3/2013 | Liu et al. |
| 2014/0056980 | A1 | 2/2014 | Oliveira Varum et al. |
| 2015/0125525 | A1 | 5/2015 | Bravo Gonzalez et al. |
| 2015/0132380 | A1 | 5/2015 | Bravo Gonzalez et al. |
| 2016/0250232 | A1 | 9/2016 | Varum et al. |
| 2017/0035698 | A1 | 2/2017 | Oliveira Varum et al. |
| 2017/0266117 | A1 | 9/2017 | Oliveira Varum et al. |

FOREIGN PATENT DOCUMENTS

| | | | |
|---|---|---|---|
| EP | 0 343 993 A1 | | 11/1989 |
| EP | 0 502 032 A1 | | 9/1992 |
| EP | 3 189 830 | | 7/2017 |
| EP | 3 278 792 | | 2/2018 |
| EP | 2 844 220 | | 1/2019 |
| GB | 2 367 002 A | | 3/2002 |
| JP | 52091419 | * | 8/1977 |
| JP | 2008-21429 | | 9/2008 |
| JP | 2008-543929 | | 12/2008 |
| JP | 2010-526110 | | 7/2010 |
| JP | 2012-153724 | | 8/2012 |
| WO | 91/07172 | | 5/1991 |
| WO | WO 91/07949 A1 | | 6/1991 |
| WO | WO 96/36321 A1 | | 11/1996 |
| WO | WO 99/21536 A1 | | 5/1999 |
| WO | WO 99/25325 A1 | | 5/1999 |
| WO | WO 01/76562 A1 | | 10/2001 |
| WO | WO 03/068196 A1 | | 8/2003 |
| WO | WO 2004/052339 A1 | | 6/2004 |
| WO | 2004/058228 | | 7/2004 |
| WO | WO 2007/122374 A2 | | 11/2007 |
| WO | WO 2008/135090 | * | 11/2008 |
| WO | WO 2008/135090 A1 | | 11/2008 |
| WO | 2009/138716 | | 11/2009 |
| WO | 2012/075015 | | 6/2012 |
| WO | 2013/035081 | | 3/2013 |
| WO | 2013/164315 | | 11/2013 |
| WO | 2013/164316 | | 11/2013 |

OTHER PUBLICATIONS

International Search Report and Written Opinion dated Jul. 10, 2013 in PCT/EP2013/058923.

Masataka Katsuma, et al., "Studies on lactulose formulations for colon-specific drug delivery" International Journal of Pharmaceutics, vol. 249, No. 1-2, XP055033720, Dec. 1, 2002, pp. 33-43.

Frederick Esseku, et al., "Bacteria and pH-Sensitive Polysaccharide-Polymer Films for Colon Targeted Delivery" Critical Reviews in Therapeutic Drug Carrier Systems, vol. 28, No. 5, XP009161434, 2011, pp. 395-445.

Snezana Milojevic, et al., "Amylose as a coating for drug delivery to the colon: Preparation and in vitro evaluation using 5-aminosalicylic acid pellets" Journal of Controlled Release, vol. 38, 1996, pp. 75-84.

A. Akhgari, et al., "Permeability and swelling studies on free films containing inulin in combination with different polymethacrylates aimed for colonic drug delivery" European Journal of Pharmaceutical Sciences, vol. 28, Mar. 2006, pp. 307-314.

Heini Kari, "An investigation of combined pH- and bacterially-triggered oral colon targeted drug delivery system" Seminar Abstract, Sep. 2, 2009, 6 Pages.

Fang Liu, et al., "A novel concept in enteric coating: A double-coating system providing rapid drug release in the proximal small intestine" Journal of Controlled Release, vol. 133, 2009, pp. 119-124.

Fang Liu, et al., "SEM/EDX and confocal microscopy analysis of novel and conventional enteric-coated systems" International Journal of Pharmaceutics, vol. 369, 2009, pp. 72-78.

Fang Liu, et al., "A novel double-coating approach for improved pH-triggered delivery to the ileo-colonic region of the gastrointestinal tract" European Journal Pharmaceutics and Biopharmaceutics, vol. 74, 2010, pp. 311-315.

Karrout "Innovative Drug Delivery System for colon targeting" 2008.

International Search Report dated Jul. 17, 2014 in International Application No. PCT/EP2013/072648, filed Oct. 29, 2013.

Written Opinion dated Jul. 17, 2014 in International Application No. PCT/EP2013/072648, filed Oct. 29, 2013.

Bozdag, et al., S.T.P. Pharma Sciences; 1999, 9(4):321-327.

Eudragit® (Evonik Industries GmbH, Darmstadt, Alemania; sin fecha) pp. 1-15; obtained Apr. 20, 2020, from the Internet URL: https://healthcare.evonik.com/sites/lists/NC/DocumentsHC/Evonik-Eudragit_brochure.pdf.

Fallingborg, J., Dan. Med. Bull; 1999; 46(3):183-196; Submitting Abstract.

Jantratid et al, Pharmaceutical Research 2008, 25(7):1663-1676; Submitting Abstract.

Liu et al., Journal of Food Engineering; 2006, 73(3):203-209; Submitting Abstract.

Liu et al., European Journal of Pharmaceutics and Biopharmaceutics, 2010. 74(2):311-315, Submitting Abstract.

McCconnell et al., International Journal of Pharmaceutics; 2008, 364(2):213-226; Submitting Abstract.

Olivia et al. (2005), Arteriosclerosis, Thrombosis and Vascular Biology; 2005, 25(2):411-417; Submitting Abstract.

Office Action dated Oct. 20, 2020 in U.S. Appl. No. 16/823,094, 15 pages.

"Cellulose Acetate Phthalate", Handbook of Pharmaceutical Excipients, 1983, 5th edition, ed. Raymond C. Rowe, Paul J. Sheskey, Sian C. Owen; monograph, pp. 145-147.

"Dibutyl Phthalate", Handbook of Pharmaceutical Excipients, 1983, 5th edition, ed. Raymond C. Rowem Paul J. Sheskey, Sian C. Owen; monograph, pp. 234-235.

"Hypromellose Acetate Succinate", Hanbook of Pharmaceutical Excipients, 1983, 5th edition, ed. Raymond C. Rowe, Paul J. Sheskey, Sian C. Owen; monograph, pp. 350-353.

"Hypromellose Phthalate", Hanbook of Pharmaceutical Excipients, 1983, 5th edition, ed. Raymond C. Rowe, Paul J. Sheskey, Sian C. Owen; monograph, pp. 354-358.

"Polymethacrylates", Handbook of Pharmaceutical Excipients, 1983, 5th edition, ed. Raymond C. Rowe, Paul J. Sheskey, Sian C. Owen; monograph, pp. 553-560.

(56) References Cited

OTHER PUBLICATIONS

"Polyvinyl Acetate Phthalate", Handbook of Pharmaceutical Excipients, 1983, 5th edition, ed. Raymond C. Rowe, Paul J. Sheskey, SIan C. Owen; monograph, pp. 589-591.

* cited by examiner

DELAYED RELEASE DRUG FORMULATION

The present application is a continuation of U.S. application Ser. No. 14/066,054 filed Oct. 29, 2013, which is pending, which is a continuation-in-part of PCT/EP2013/058921 filed Apr. 29, 2013 and PCT/EP2013/058923 filed Apr. 29, 2013, and claims the benefit of U.S. application Ser. No. 61/640,217 filed Apr. 30, 2012.

The present invention relates to a delayed release formulation with a core comprising a drug and a coating for providing delaying release of the drug until the colon. In particular, it relates to use of an isolation layer to accelerate initial release of the drug once the intestine is reached.

The targeting of drugs to the intestine is well known and has been known for over one hundred years. Commonly, the target of the drugs is the small intestine although the colon can be utilised as a means of achieving local therapy or systemic treatment. The requirements for the coatings on the drugs are different depending on the target site. In order to reach the colon, it is necessary for the drugs to pass through the small intestine, and therefore it is a requirement that a delayed release coating intended to release the drug in the colon does not release the drug in the small intestine.

Coated products for release in the small intestine commonly use polymer coatings which dissolve or disintegrate in a pH dependent manner. In the low pH environment of the stomach, the polymer coating is insoluble. However, on reaching the small intestine, the pH rises to 5 and above and the polymeric coating dissolves or disintegrates. A commonly used coating is one containing ionisable carboxylic groups. At higher pH levels, the carboxylic groups ionize, allowing the polymer coatings to disintegrate or dissolve. Common polymers of this type which are used include Eudragit® L and Eudragit® S.

Various methods of improving the release in the small intestine by ensuring an earlier release of the drug are known. US2008/0200482 is one of a number of references which discloses partially neutralizing the carboxylic groups in order to reduce the pH at which disintegration occurs. WO2008/135090 discloses a tablet with an inner coat of partially neutralized material and an outer coat with less or no neutralization. This is said to result in disintegration at an earlier time point when transferred from the stomach.

Release of drugs in the colon typically requires an alternative approach. The colon is susceptible to a number of disease states, including inflammatory bowel disease, irritable bowel syndrome, constipation, diarrhoea, infection and carcinoma. In such conditions, drug targeting to the colon would maximise the therapeutic effectiveness of the treatment. The colon can also be utilised as a portal for the entry of drugs into the systemic circulation. Various formulations have been developed for colonic drug delivery, including pro-drugs as well as formulated dosage forms, with the latter being more popular since the concept once proved can be applied to other drugs.

The higher bacterial population in the colon has also been exploited in developing colonic drug delivery dosage forms through the use, as carrier materials, of naturally occurring polysaccharides that constitute substrates for the numerous enzymes of the resident colonic bacteria. These materials are able to pass through the upper gastrointestinal regions intact but are digested upon entry into the colon. Those studied so far include amylose, pectin, chitosan and galactomannan.

One major attraction of using polysaccharides in this bacterial enzyme approach to colonic drug delivery is that materials used are of food grade and so would be safe for use in humans. They are usually applied as coatings or incorporated in the core material as a matrix carrier, and their digestion on entry into the colon by the colonic bacterial enzymes leads to the release of the drug load. An example of such a formulation, which employs an amylose coating, is disclosed in EP0343993A (BTG International Limited).

EP0502032A (British Technology Group Ltd) teaches the use of an outer coating comprising a film forming cellulose or acrylate polymer material and amorphous amylose for a tablet comprising an active compound. The polymer material used is a pH independent release polymer material.

An article in Journal of Controlled Release (Milojevic et al; 38; (1996); 75-84) reports the results of investigations concerning the incorporation of a range of insoluble polymers into an amylose coating in order to control amylose swelling. A range of cellulose and acrylate based co-polymers are assessed, and a commercially available ethyl cellulose (Ethocel®) is found to control the swelling most effectively. A pH dependent soluble coating of Eudragit® L100 is employed but only in a multi-layer system comprising a bioactive coated with an inner coating of amylose and then an outer coating of Eudragit® L100.

A further amylose-based coating composition is disclosed in WO99/21536A (BTG International Limited). The coating composition comprises a mixture of amylose and a water insoluble pH independent film-forming polymer which is formed from a water-insoluble cellulosic or acrylate polymer material.

WO99/25325A (BTG International Limited) also discloses a delayed release coating comprising amylose and (preferably) ethyl cellulose or alternatively an insoluble acrylate polymer. The coating composition also includes a plasticiser and the method finds particular application in the preparation of dosage forms comprising active materials that are unstable at temperatures in excess of 60° C., as the composition is formed at lower temperatures than this.

WO03/068196A (Alizyme Therapeutics Ltd) discloses a specific delayed release coating for the bioactive prednisolone sodium metasulphobenzoate comprising glassy amylose, ethyl cellulose and dibutyl sebacate.

The use of polysaccharides other than amorphous amylose in a delayed release coating is disclosed in GB2367002 (British Sugar PLC). Examples include guar gum, karaya gum, gum tragacanth and xanthan gum. Microparticles of these polysaccharides are dispersed in a water-insoluble film-forming polymer matrix formed for example from a cellulose derivative, an acrylic polymer or a lignin.

WO01/76562A (Tampereen Patenttitoimisto Oy) discloses a per oral pharmaceutical formulation containing a drug and a chitosan (a polysaccharide obtained from chitin) for controlling its release. The drug and the chitosan are mixed into a homogeneous mechanical powder mixture which is granulated and then optionally tableted. The granulation may be performed with an enteric polymer (such as a copolymer of methacrylic acid) or the granules may be provided with a porous enteric coating.

WO2004/052339A (Salvona LLC) discloses a pH dependent drug release system which is a free-flowing powder of solid hydrophobic nano-spheres comprising a drug encapsulated in a pH-sensitive micro-sphere. The nano-spheres are formed from the drug in combination with a wax material, and the pH-sensitive micro-sphere formed from a pH-sensitive polymer (such as a Eudragit® polymer) in combination with a water-sensitive material such as a polysaccharide.

An article in the European Journal of Pharmaceutical Sciences (Akhgari et al; 28; Mar. 2006; 307-314) reports the results of investigations into the use of certain polymethacrylate polymers to, inter alia, control the swelling of inulin. The polymethacrylate polymers tested were Eudragit® RS; Eudragit® RL; 1:1 mixtures of Eudragit® RS and Eudragit® RL; Eudragit® FS; and 1:1 mixtures of Eudragit® RS and Eudragit® S.

U.S. Pat. No. 5,422,121 (Röhm GmbH) discloses an oral dosage form having a core containing at least one active ingredient enclosed within a shell material which comprises a polysaccharide that decomposes in the colon in admixture with a film-forming polymer. The ratio by weight of polysaccharide to film forming polymer is from 1:2 to 5:1, preferably from 1:1 to 4:1. Premature diffusion of the active ingredient from the core can be suppressed using a gastric resistant isolating layer. The reference exemplifies inter alia tablets having an inner isolating layer of Eudragit® L30D with an outer layer comprising Eudragit® L30D and guar gum (Example 2).

WO96/36321A discloses an oral dosage form comprising a core containing bisacodyl, and an enteric polymer coating for the core, the coating comprising at least one inner coating layer and an outer coating layer. The or each the inner coating layer is an enteric polymer that begins to dissolve in an aqueous medium at a pH from about 5 to about 6.3, and the outer coating layer is an enteric polymer that begins to dissolve in an aqueous medium at a pH from about 6.8 to about 7.2. The enteric polymer coating materials for the inner layer(s) are selected from the group consisting of cellulose acetate phthalate; cellulose acetate trimellitate; hydroxypropyl methylcellulose phthalate; hydroxypropyl methylcellulose acetate succinate; polyvinyl acetate phthalate; poly(methacrylic acid, methyl methacrylate) 1:1; poly(methacrylic acid, ethyl acrylate) 1:1; and compatible mixtures thereof.

An abstract entitled "*An investigation of combined pH- and bacterially-triggered oral colon targeted drug delivery system*" by Heini Kari of the Department of Pharmaceutical Technology in the Faculty of Pharmacy at University of Helsinki dated 2 Sep. 2009 discloses tablet formulations having a heat treated polysaccharide/Eudragit® S coating for colonic release and an HPMC sub-coating. Very few details of the formulations are provided in the abstract. For example, the identity of the polysaccharide, the proportions of the polysaccharide and Eudragit® S in the coating and the identity and proportions of any excipients are not provided. However, it is disclosed that tablets with heat treated coatings, and especially with HPMC sub-coatings, had "better" drug release profiles than completely organic coatings in the conventional dissolution tests in the presence of one enzyme. No details of how or why the drug release profile is better are provided although the author speculates that the reason may be because of a more uniform coating structure in which polysaccharide granules are not present.

In a paper entitled "*A novel concept in enteric coating: A double-coating system providing rapid drug release in the proximal small intestine*" by Liu et al (J. Cont. Rel. 133 (2009) 119-124), it is disclosed that release of prednisolone from tablets having a double coating system comprising an inner coat of partially neutralised Eudragit® L 30 D-55 and organic acid, and an outer coat of standard Eudragit® L 30 D-55 was accelerated in conditions resembling the upper small intestine. The inner coat was neutralised to pH 5.6 in the presence of 10% citric acid or adipic acid. The tablets did not have an isolation layer.

In a paper entitled "*SEM/EDX and confocal microscopy analysis of novel and conventional enteric-coated systems*" by Liu et al (Int. J. Pharm. 369 (2009) 72-78), it is disclosed that prednisolone was released more rapidly from tablets coated with an inner coat of partially neutralised Eudragit® L 30 D-55 and organic acid, and an outer coat of standard Eudragit® L 30 D-55, than from tablets coated with Eudragit® L 30 D-55 alone with or without a subcoat of HPMC. The double coated tablets did not have a subcoat of HPMC although the authors of the paper observed that drug release from the tablets having the single enteric coat with the HPMC subcoat was faster than from the single enteric coated tablets without the subcoat.

It is also reported in a paper entitled "*A novel double-coating approach for improved pH-triggered delivery to the ileo-colonic region of the gastrointestinal tract*" by Liu et al (Eur. J. Pharm. Biopharm. 74 (2010) 311-315), that initial release in vitro (in Krebs buffer (pH 7.4) after 2 h in 0.1 M HCl) of prednisolone was faster from tablets coated with a coating system comprising an inner layer of partially neutralised Eudragit S and buffer agent and an outer layer of standard Eudragit S, than from tablets without the inner layer. None of the tablets disclosed in this paper had an isolation layer.

WO2007/122374A discloses a colonic drug delivery formulation in which a mixture of a pH dependent film forming polymeric material and a polysaccharide such as starch is used. Although it is known that this formulation shows delayed release followed by a relatively quick release of the drug, it would be preferred if the drug release was even quicker in the colon, after the triggers are initiated.

In accordance with a first aspect of the present invention, there is provided an isolation layer for use in accelerating drug release in the intestine of a subject from a delayed release drug formulation for oral administration to said subject, said formulation comprising:

a core comprising said drug;

said isolation layer coating said core; and an outer coating for providing intestinal release of said drug, said outer coating comprising an outer layer and an inner layer, wherein said outer layer comprises a pH dependently soluble polymeric material which has a pH threshold at about pH 5 or above, and wherein the inner layer comprises a soluble polymeric material which is soluble in intestinal fluid or gastrointestinal fluid, said soluble polymeric material being selected from the group consisting of a polycarboxylic acid polymer that is at least partially neutralised, and a non-ionic polymer, provided that, where said soluble polymeric material is a non-ionic polymer, said inner layer comprises at least one additive selected from a buffer agent and a base.

The Inventors have discovered that the use of an isolation layer in such formulations accelerates initial release of the drug once the formulations are exposed to pH conditions found in the colon. This result was entirely unexpected. The Inventors introduced the isolation for the purpose of preventing erosion at the edges of the tablets prior to coating. They fully expected the additional layer to further delay release in line with conventional wisdom. However, they were surprised to observe that, rather than delay initial release, the isolation layer actually accelerated initial once the coated tablets were exposed to colonic pH. The Inventors are not aware of any literature which could have predicted such a result.

The isolation layer also improves the stability of the formulations during storage by preventing deceleration of initial release over time.

In preferred embodiments, the isolation layer comprises a film-forming non-ionic polymer, such as HPMC or PVA, and typically has a thickness from about 1 mg polymer/cm$^2$ to about 5 mg polymer/cm$^2$.

In some preferred embodiments, the pH dependently soluble polymeric material is the sole film forming polymer in the outer layer. However, in other preferred embodiments, the outer layer has a mixture of a digestible (or "first") polymeric material susceptible to attack by colonic bacteria, e.g. a polysaccharide, and the pH dependently soluble (or "second") polymeric material.

The soluble (or "third") polymeric material that is soluble in intestinal fluid or gastrointestinal fluid is typically a partially or fully neutralised polycarboxylic acid polymer. In these embodiments, the pH dependently soluble (or second) polymer material is typically a polycarboxylic acid polymer of the same type as the polymer of the inner layer but either non-neutralised or partially neutralised to a lower extent than the soluble (or third) polymeric material.

Formulations according to embodiments of the present invention have superior colonic-release properties over comparative coatings designed for site-specific release in the colon. In this connection, drug release from formulations according to embodiments of the present invention appears to be accelerated in the colon when compared to comparative colonic release formulations. The Inventors are confident that other formulations within the scope of the invention should also have superior release properties over comparative coatings designed for site-specific release in the small intestine, and proximal small intestine in particular. Broadly speaking, the region of the intestine in which initial release occurs can be controlled by the choice of pH dependently soluble polymeric material.

Without wishing to be bound by any particular theory, the Inventors believe that, once intestinal fluid or gastrointestinal fluid penetrates the outer layer, the inner layer begins to dissolve before the outer layer to form a fluid region between the core and the outer layer. The fluid region not only facilitates dissolution and/or disintegration of the outer layer from the inside, but also softens and begins to break up the core so that, when the outer layer degrades, the drug is released from the core more quickly.

In some preferred embodiments, the further acceleration provided by the isolation layer is very likely due to the barrier effect between an acidic core (e.g. a core containing 5ASA) and an alkaline inner layer. In these embodiments, the Inventors believe that the isolation layer prevents or limits the effect of the acidic drug on the alkaline inner layer, not compromising and/or competing for the alkalinity which promotes the accelerated dissolution of the outer layer.

It is preferred that the digestible (or first) polymeric material comprises at least one polysaccharide selected from the group consisting of starch; amylose; amylopectin; chitosan; chondroitin sulphate; cyclodextrin; dextran; pullulan; carrageenan; scleroglucan; chitin; curdulan and levan. It is particularly preferred that the digestible (or first) polymeric material is starch.

In preferred embodiments, the pH dependently soluble (or second) polymeric material is an anionic polymeric material, and more preferably an anionic copolymer of a (meth)acrylic acid and a (meth)acrylic acid alkyl ester.

The soluble (or third) polymeric material of the inner layer is preferably an anionic polymeric material and more preferably an at least partially neutralised, preferably fully neutralised, copolymer of a (meth)acrylic acid and a (meth)acrylic acid alkyl ester.

In a preferred embodiment, the second polymeric material is the same type of copolymer of a (meth)acrylic acid and a (meth)acrylic acid alkyl ester as the third polymeric material prior to neutralisation.

In a particularly favourable embodiment, the present invention relates to a delayed release drug formulation comprising a core comprising a drug, an isolation layer for the core and a delayed release coating for the isolated core, the delayed release coating comprising an outer layer and an inner layer, wherein the outer layer comprises a mixture of starch and a copolymer of a (meth)acrylic acid and a (meth)acrylic acid $C_{1-4}$ alkyl ester; and the inner layer comprises a fully neutralized copolymer of a (meth)acrylic acid and a (meth)acrylic acid $C_{1-4}$ alkyl ester.

Some materials that are susceptible to attack by colonic bacteria, e.g. amylose, swell when exposed to aqueous fluid, e.g. gastrointestinal fluid. Such swelling is undesirable since it results typically in premature release of the drug. The swelling is controlled by the inclusion of a pH dependent material having a pH threshold of pH 5 or above.

A further technical advantage of the present invention (compared, for example, to the formulation disclosed in WO01/76562A) is that substantially no drug is released for an extended period (that is, whilst the coating is intact and is being dissolved/disintegrated), following which the drug is released relatively quickly. This is in contrast to homogeneous tablets from which the drug release profile is gradual from the outset rather than delayed then pulsatile.

A yet further technical advantage of the present invention compared to WO2007/122374A is accelerated release of the drug once the formulation is exposed to the conditions of the colonic environment.

Isolation Layer

The isolation layer typically accelerates initial release of the drug in the intestine from the present formulation compared to an equivalent formulation without the isolation layer.

By "accelerating release", the Inventors mean reducing the delay before initial release of the drug once exposed to intestinal conditions. This delay is referred to as the lag time or $T_{lag}$.

The present invention has particular application in accelerating release in the colon. According to these embodiments of the present invention, the lag time ($T_{lag}$) in vitro in Krebs buffer at pH 7.4 after 2 h at 0.1M HCl is typically reduced by at least 10%, preferably by at least 20%, more preferably by at least 30% and most preferably by at least 40%. In absolute terms, the lag time ($T_{lag}$) in vitro in Krebs buffer at pH 7.4 after 2 h at 0.1M HCl is typically reduced by at least 10 minutes, preferably by at least 20 minutes, more preferably by at least 30 minutes, and most preferably by at least 45 minutes.

In other embodiments, the isolation layer is for use in accelerating drug release in the small intestine, and particularly in the proximal small intestine, of the subject. According to these embodiments of the present invention, the lag time ($T_{lag}$) in vitro in a buffered solution at an appropriate pH (e.g. pH 5.5 for the proximal small intestine or pH 6.8 to 7.2 for the ileum) after 2 h at 0.1M HCl is typically similar to that indicated above at pH 7.4.

The polymeric material of the isolation layer is preferably present in the isolation layer in a total amount from about 1 mg polymer/cm$^2$ to about 5 mg polymer/cm$^2$, preferably from about 2 mg polymer/cm$^2$ to about 4 mg polymer/cm$^2$, more preferably from about 2.5 mg polymer/cm$^2$ to about 3.5 mg polymer/cm$^2$, and most preferably of about 3 mg polymer/cm², as such coating amounts tend to provide optimum improvement in acceleration of initial release.

The thickness of the isolation layer is typically from about 5 μm to about 100 μm, preferably from about 10 μm to about 60 μm, and most preferably from about 20 μm to about 40 μm. Such coating thicknesses typically provide optimum improvement in acceleration of initial release.

By "thickness" of a layer or coating, the Inventors are referring to the perpendicular dimension between the inner and outer surfaces of the layer or coating in question. The values provided herein regarding layer or coating thickness are a mean average of the thickness measured at different points of a cross-section of the coated dosage form, including at the edges where the layer or coating is typically thinner.

The thickness of a layer or coating on an oral dosage form such as a tablet, is generally measured by subjecting the cross section of the dosage form to scanning electron microscopy (SEM) and then by using the measurement software of the SEM instrument (i.e. Phenom SEM measurement software) or any other measurement software like MeasureIT from Olympus Soft Imaging Solutions GmbH. However, SEM may not be specific enough in some cases, including in cases where adjacent layers cannot be distinguished properly, or where the typical margin of error in SEM (about 5 to 10%) is not acceptable. In such cases, the thickness of the coating or layer to be distinguished can be determined precisely using atomic force microscopy (AFM) or terahertz pulsed spectroscopy and imaging (TPI). A method of using TPI to measure the thickness of a layer in a tablet is described in the Journal of Pharmacy and Pharmacology (2007), 59: 209-223.

As indicated above, the isolation layer typically comprises at least one non-ionic polymer. Suitable polymers include at least one polymer selected from the group consisting of methylcellulose (MC); hydroxypropyl cellulose (HPC); hydroxypropyl methylcellulose (HPMC); poly(ethylene oxide)-graft-polyvinyl alcohol; polyvinylpyrrolidone (PVP); and polyvinyl alcohol (PVA).

In some embodiments, the isolation layer does not need to include a plasticizer. However, in other embodiments, the isolation layer can additionally comprise at least one plasticizer to provide better film quality. Any suitable plasticizers may be used, including triethyl citrate (TEC) and polyethylene glycol (PEG). The total amount of plasticizer(s) in the layer is typically from about 5 wt % to about 50 wt %, e.g. from about 10 wt % to about 30 wt %. In some embodiments, the total amount of plasticizer may be about 20 wt %.

In some preferred embodiments, the isolation layer comprises HPMC. In other preferred embodiments, the isolation layer comprises PVA.

The non-ionic polymer is typically present in the isolation layer as the sole film-forming polymeric material.

Digestible (or First) Polymeric Material

The digestible (or first) polymeric material typically comprises a polysaccharide, preferably containing a plurality of hexose units. In a preferred embodiment, the polysaccharide is at least one polysaccharide selected from the group consisting of starch; amylose; amylopectin; chitosan; chondroitin sulphate; cyclodextrin; dextran; pullulan; carrageenan; scleroglucan; chitin; curdulan and levan. It is further preferred that the polysaccharide is starch, amylose or amylopectin, most preferably starch.

The person skilled in the art is capable of determining whether a polymeric material is susceptible to attack by colonic bacteria using techniques comprising part of the common general knowledge. For example, a pre-determined amount of a given material could be exposed to an assay containing an enzyme from a bacterium found in the colon and the change in weight of the material over time may be measured.

The polysaccharide is preferably starch. Starches are usually extracted from natural sources such as cereals; pulses; and tubers. Suitable starches for use in the present invention are typically food grade starches and include rice starch; wheat starch; corn (or maize) starch; pea starch; potato starch; sweet potato starch; tapioca starch; sorghum starch; sago starch; and arrow root starch. The use of maize starch is exemplified below.

Starch is typically a mixture of two different polysaccharides, namely amylose and amylopectin. Different starches may have different proportions of these two polysaccharides. Most natural (unmodified) maize starches have from about 20 wt % to about 30 wt % amylose with the remainder being at least substantially made up of amylopectin. Starches suitable for use in the present invention typically have at least 0.1 wt %, e.g. at least 10% or 15%, preferably at least 35 wt %, amylose.

"High amylose" starches, i.e. starches having at least 50 wt % amylose, are suitable. Particularly suitable starches have from about 55 wt % to about 75 wt %, e.g. about 60 wt % or about 70 wt % amylose. In particular, starches having from about 50 wt % to about 60 wt % amylose are also suitable, Starches suitable for use in the present invention may have up to 100% amylopectin, more typically from about 0.1 wt % to about 99.9 wt % amylopectin. "Low amylose" starches, i.e. starches having no more than 50 wt % amylose and at least 50 wt % amylopectin, e.g. up to 75 wt % amylopectin and even as much as up to 99 wt % amylopectin, are still suitable. The starch may be, for example, unmodified waxy corn starch. This typically comprises about 100% amylopectin.

Preferred starches have no more than 50 wt % amylopectin. As indicated above, particularly suitable starches are "high amylose" starches which have from about 25 wt % to about 45 wt % amylopectin, e.g. about 30 wt % or about 40 wt % amylopectin. In particular, starches having from about 40 wt % to about 50 wt % amylopectin are also suitable.

The person skilled in the art is capable of determining the relative proportions of amylose and amylopectin in any given starch. For example, near-infrared ("NIR") spectroscopy could be used to determine the amylose and amylopectin content of a starch using calibration curves obtained by NIR using laboratory-produced mixtures of known amounts of these two components. Further, starch could be hydrolysed to glucose using amyloglucosidase. A series of phosphorylation and oxidation reactions catalysed by enzymes result in the formation of reduced nicotinamide adenine dinucleotide phosphate ("NADPH"). The quantity of NADPH formed is stoichiometric with the original glucose content. Suitable test kits for this procedure are available (e.g., R-Biopharm GmbH, Germany). Another method that could be used involves subjecting the coating to digestion by bacterial enzymes, e.g. α-amylase, to produce short chain fatty acids ("SCFA") which can be quantified by gas-liquid chromatography using a capillary column.

Preferred starches have amylose in its glassy form although amylose in its amorphous form may also be used in conjunction with the present invention.

Preferred starches are "off-the-shelf" starches, i.e. starches which require no processing prior to use in the context of the present invention. Examples of particularly suitable "high amylose" starches include Hylon™ VII (National Starch, Germany), Eurylon™ 6 (or VI) or Amylo NI-460 or Amylo N-400 (Roquette, Lestrem, France), or Amylogel 03003 (Cargill, Minneapolis, USA) all of which are examples of a maize starch having from about 50 wt % to about 75 wt % amylose.

pH Dependently Soluble (or Second) Polymeric Material

The present invention involves the use of a pH dependently soluble (or second) polymeric material that dissolves in a pH dependent manner. The second material is a film forming polymer that is pH sensitive, i.e. has a "pH threshold" which is the pH below which it is insoluble in aqueous media and at or above which it is soluble in aqueous media. Thus, the pH of the surrounding medium triggers dissolution of the second polymeric material and none (or essentially none) of the second polymeric material dissolves below the pH threshold. Once the pH of the surrounding medium reaches (or exceeds) the pH threshold, the second polymeric material becomes soluble.

Throughout the specification, the term "insoluble" is used to mean that 1 g of a polymeric material requires more than 10,000 ml of solvent or "surrounding medium" to dissolve at a given pH. In addition, the term "soluble" is used to mean that 1 g of a polymeric material requires less than 10,000 ml, preferably less than 5,000 ml, more preferably less than 1000 ml, even more preferably less than 100 ml or 10 ml of solvent or surrounding medium to dissolve at a given pH.

By "surrounding medium", the Inventors mean gastric fluid and intestinal fluid, or an aqueous solution designed to recreate in vitro gastric fluid or intestinal fluid.

The normal pH of gastric juice is usually in the range of pH 1 to 3. The second polymeric material is insoluble below pH 5 and soluble at about pH 5 or above and, thus, is usually insoluble in gastric juice. Such a material may be referred to as a gastro-resistant material or an "enteric" material.

The second polymeric material has a pH threshold of pH 5 or above, e.g. about pH 5.5 or above, preferably about pH 6 or above and more preferably about pH 6.5 or above. The second polymeric material typically has a pH threshold of no more than about pH 8, e.g. no more than about pH 7.5 and preferably no more than about pH 7.2. Preferably, the second polymeric material has a pH threshold within the range of pH found in intestinal fluid. The pH of intestinal fluid may vary from one person to the next, but in healthy humans is generally from about pH 5 to 6 in the duodenum, from about 6 to 8 in the jejunum, from about 7 to 8 in the ileum, and from about 6 to 8 in the colon.

For embodiments in which initial release is intended for the small intestine, the second polymeric material preferably has a pH threshold of about pH 5.5, and more preferably has a pH threshold of about pH 6. For embodiments in which initial release is intended for the colon, the second polymeric material preferably has a pH threshold of about pH 6.5, and more preferably has a pH threshold of about pH 7.

The pH threshold at which a material becomes soluble may be determined by a simple titration technique which would be part of the common general knowledge to the person skilled in the art.

The second polymeric material is typically a film-forming polymeric material such as a polymethacrylate polymer, a cellulose polymer or a polyvinyl-based polymer. Examples of suitable cellulose polymers include cellulose acetate phthalate (CAP); cellulose acetate trimellitate (CAT); Hydroxypropylmethylcellulose phthalate (HPMCP) and hydroxypropylmethylcellulose acetate succinate (HPMC-AS). Examples of suitable polyvinyl-based polymers include polyvinyl acetate phthalate (PVAP).

The second material is preferably an "anionic" polymeric material, i.e. a polymeric material containing groups that are ionisable in aqueous media to form anions (see below), and more preferably a co-polymer of a (meth)acrylic acid and a (meth)acrylic acid $C_{1-4}$ alkyl ester, for example, a copolymer of methacrylic acid and methacrylic acid methyl ester. Such a polymer is known as a poly(methacrylic acid/methyl methacrylate) co-polymer. Suitable examples of such co-polymers are usually anionic and not sustained release polymethacrylates. The ratio of carboxylic acid groups to methyl ester groups (the "acid:ester ratio") in these co-polymers determines the pH at which the co-polymer is soluble. The acid:ester ratio may be from about 2:1 to about 1:3, e.g. about 1:1 or, preferably, about 1:2. The molecular weight ("MW") of preferred anionic co-polymers is usually from about 120,000 to 150,000 g/mol, preferably about 125,000 g/mol or about 135,000 g/mol.

Preferred anionic poly(methacrylic acid/methyl methacrylate) co-polymers have a molecular weight of about 125,000 g/mol. Suitable examples of such polymers have an acid:ester ratio of about 1:1 and a pH threshold of about pH 6, or have an acid:ester ratio of about 1:2 and a pH threshold of about pH 7.

A specific example of a suitable anionic poly(methacrylic acid/methyl methacrylate) co-polymer having a molecular weight of about 125,000 g/mol, an acid:ester ratio of about 1:1 and a pH threshold of about pH 6 is sold under the trade mark Eudragit® L. This polymer is available in the form of a powder (Eudragit® L 100), or as an organic solution (12.5%) (Eudragit® L 12.5).

A specific example of a suitable anionic poly(methacrylic acid/methyl methacrylate) co-polymer having a molecular weight of about 125,000 g/mol, an acid:ester ratio of about 1:2 and a pH threshold of about pH 7 is sold under the trade mark Eudragit® S. This polymer is available in the form of a powder (Eudragit® S 100) or as an organic solution (12.5%) (Eudragit® S 12.5).

The second polymeric material may be a co-polymer of methacrylic acid and ethyl acrylate. Preferred poly(methacrylic acid/ethyl acrylate) co-polymers have a molecular weight from about 300,000 to 350,000 g/mol, e.g. about 320,000 g/mol. Suitable examples of such co-polymers have an acid:ester ratio of about 1:1 and a pH threshold of about pH 5.5.

A specific example of a suitable anionic poly(methacrylic acid/ethyl acrylate) co-polymer is available in the form of a powder and sold under the trade mark Eudragit® L 100-55, or in the form of an aqueous dispersion (30%) and sold under the trade mark Eudragit® L 30 D-55.

The second polymeric material may be a co-polymer of methyl acrylate, methyl methacrylate and methacrylic acid. Preferred poly(methyl acrylate/methyl methacrylate/methacrylic acid) co-polymers have a molecular weight from about 250,000 to about 300,000 g/mol, e.g. about 280,000 g/mol. Suitable examples of such co-polymers have a methyl acrylate:methyl methacrylate:methacrylic acid ratio of about 7:3:1 thereby providing an acid:ester ratio of about 1:10 and a pH threshold of about pH 7.

A specific example of a suitable anionic poly(methyl acrylate/methyl methacrylate/ethyl acrylate) co-polymer is available in the form of an aqueous dispersion (30%) and is sold under the trade mark Eudragit® FS 30 D.

The Eudragit® co-polymers are manufactured and/or distributed by Evonik GmbH, Darmstadt, Germany.

Mixtures of film forming polymer materials may be used as appropriate. For example, the second polymeric material may be a blend of at least two different polymers having a pH threshold of about pH 5 and above. Preferably, the polymers in the blend are different polymethacrylate polymers. In embodiments where the second polymeric material is a blend of two different polymers having a pH threshold of about pH 5 or above, the polymers may be present in the blend in a polymer weight ratio from about 1:99 to about 99:1, e.g. from about 10:90 to about 90:10, or from 25:75 to about 75:25, or from about 40:60 to about 60:40, for example about 50:50.

An example of a suitable mixture would include a mixture, e.g. a 1:1 mixture, of Eudragit® L and Eudragit® S. A further example would include a blend, e.g. a 50:50 blend, of Eudragit S and Eudragit FS.

For the avoidance of doubt, the terms "mixture" and "blend" in the context of mixtures or blends of polymers forming the second polymeric material, are used herein interchangeably.

However, the use of a particular film forming polymer material, e.g. a poly(methacrylic acid/methyl methacrylate) co-polymer, alone is preferred. The use of Eudragit® S alone as the second polymeric material is particularly preferred for colonic release formulations.

Outer Layer

In some preferred embodiments, the pH dependently soluble (or second) polymeric material(s) is/are present in the outer layer as the sole film-forming polymeric material(s). In other preferred embodiments, the pH dependently soluble (or second) polymeric material(s) is/are present in the outer layer in admixture with the digestible (or first) polymeric material(s) which is susceptible to attack by colonic bacteria.

In embodiments in which the outer layer comprises a mixture of first and second polymeric materials, the proportion of the first polymeric material to the second polymeric material is typically at least 1:99, e.g. at least 10:90 and preferably at least 25:75. The proportion is typically no more than 99:1, e.g. no more than 75:25 and preferably no more than 60:40. In some embodiments, the proportion may be no more than 35:65. In some preferred embodiments, the proportion is from 10:90 to 75:25, e.g. from 10:90 to 60:40 and preferably from 25:75 to 60:40. In some particularly preferred embodiments, the proportion is from 15:85 to 35:65, e.g. from 25:75 to 35:65 and preferably about 30:70. In other particularly preferred embodiments, the proportion is from 40:60 to about 60:40, e.g. about 50:50.

The mixture of first and second polymeric materials is preferably substantially homogenous.

Optionally, conventional excipients such as those excipients selected from plasticisers for film formation (for example, triethyl citrate), anti-tack agents (such as glyceryl monostearate or GMS) and surfactants (such as polysorbate 80), may be included in amounts up to 30 wt % of the final composition of the outer coating preparation.

The thickness of the outer coating of the core is typically from about 10 μm to about 150 μm. The thickness of a specific coating will, however, depend on the composition of the coating. For example, coating thickness is directly proportional to the amount of polysaccharide in the coating. Thus, in embodiments where the coating comprises high amylose starch and Eudragit™ S at a ratio of about 30:70, the coating thickness may be from about 70 μm to about 130 μm, and preferably from about 90 μm to about 110 μm.

The coating amount of the polymeric material(s) in the outer coating is typically from about 2 mg/cm$^2$ to about 10 mg/cm$^2$, preferably from about 2 mg/cm$^2$ to about 8 mg/cm$^2$, and most preferably from about 4 mg/cm$^2$ to about 8 mg/cm$^2$, based on the dry weight of the total polymeric material. These values are particularly appropriate for cores having a diameter from about $5 \times 10^{-4}$ m to about 25 mm.

Soluble (or Third) Polymeric Material

The formulation according to the present invention additionally has an inner layer which is positioned between the isolation layer and the outer layer. The inner layer comprises a third polymeric material which may be insoluble in gastric fluid and soluble in intestinal fluid, but preferably is soluble in both gastric fluid and intestinal fluid (referred herein as gastrointestinal fluid).

By "gastric fluid", the inventors mean the aqueous fluid in the stomach of a mammal, particularly a human. The fluid contains up to about 0.1 N hydrochloric acid and substantial quantities of potassium chloride and sodium chloride, and plays a key role in digestion by activating digestive enzymes and denaturing ingested protein. Gastric acid is produced by cells lining the stomach and other cells produce bicarbonate which acts as a buffer to prevent the gastric fluid from becoming too acidic.

By "intestinal fluid", the Inventors mean the fluid in the lumen of the intestine of a mammal, particularly a human. Intestinal fluid is a pale yellow aqueous fluid secreted from glands lining the walls of the intestine. Intestinal fluid includes fluid found in the small intestine, i.e. fluid found in the duodenum (or "duodenal fluid"), fluid found in the jejunum (or "jejunal fluid") and fluid found in the ileum (or "ileal fluid"), and fluid found in the large intestine, e.g. "colonic fluid".

The skilled person can readily determine whether a polymer is soluble in gastric fluid and/or intestinal fluid. If a polymer is soluble in water (or aqueous solution), e.g. a buffer solution) at a pH from 1 to 3, then that polymer would typically be soluble in gastric fluid. Similarly if a polymer is soluble in water (or aqueous solution, e.g. a buffer solution) at a pH from 5 to 8, then that polymer would typically be soluble in intestinal fluid. Alternatively, the compositions of gastric fluid and intestinal fluid are known and may be replicated in vitro. If a polymer is soluble in artificial gastric fluid or intestinal fluid in vitro, then it would typically be soluble in gastric fluid or intestinal fluid respectively in vivo.

Any pharmacologically acceptable water soluble film forming polymers are, in principle, suitable for use as the third polymeric material. The solubility of the water soluble polymers may be dependent on pH, i.e. the third polymeric material may be a pH sensitive polymer having a pH threshold. In such embodiments, the pH threshold of the third polymeric material is less than, typically at least 0.5 pH units less than and preferably from 0.5 to 3.5 pH units less than, the pH threshold of the second polymeric material. The pH threshold of the third polymeric material is typically from about pH 4.5 to about pH 7.5.

The third polymeric material may be soluble in at least one fluid selected from gastric fluid, duodenal fluid, jejunal fluid and ileal fluid. However, in preferred embodiments, the solubility of the third polymeric material in water is not dependent on pH; at least not within the range of pH found in the intestine. In preferred embodiments, the third polymeric material is soluble in fluid at any point in the stomach and intestine, i.e. in gastrointestinal fluid.

Suitable polymers for use as the third polymeric material preferably contain groups that are ionisable in aqueous media to form anions. Such polymers are known in the art as "anionic" polymers. Suitable anionic polymers include polycarboxylic acid polymers, i.e. polymers or co-polymers that contain a plurality of carboxylic acid functional groups that are ionisable in aqueous media such as intestinal fluid, to form carboxylate anions.

In embodiments in which the third polymeric material is a polycarboxylic acid polymer, it is preferred that the third polymeric material is at least partially neutralised, i.e. that at least a portion, e.g. at least 10%, preferably at least 25%, more preferably at least 50%, and most preferably at least 90%, of the carboxylic acid groups in are the form of carboxylate anions. In particularly preferred embodiments, all of the carboxylic acid groups in the third polymeric material are in the form of carboxylate anions. Such polymers are referred to herein as "fully neutralised".

In preferred embodiments, the second and third polymeric materials are based on the same polycarboxylic acid polymer with the third polymeric material having a higher degree of neutralisation than the second polymeric material. For example, for a particular polycarboxylic acid polymer, the second polymeric material may be in non-neutralised form with the third polymeric material in partially or fully neutralised form. Alternatively, the second polymeric material may be in partially neutralised form, with the third polymeric material also in partially neutralised form (although partially neutralised to a greater extent), or in fully neutralised form.

Examples of suitable polycarboxylic acid polymers include cellulose acetate phthalate (CAP), polyvinyl acetate phthalate (PVAP), hydroxypropyl methylcellulose phthalate (HPMCP), hydroxypropyl methylcellulose acetate succinate (HPMC-AS), cellulose acetate trimellitate (CAT), xanthan gum, alginates and shellac. However, the polycarboxylic acid polymer is preferably selected from co-polymers of a (meth)acrylic acid and a (meth)acrylic acid alkyl, e.g. $C_{1-4}$ alkyl, ester and a copolymer of methacrylic acid and methacrylic acid methyl ester is particularly suitable. Such a polymer is known as a poly(methacrylic acid/methyl methacrylate) co-polymer or a "polymethacrylate". The ratio of carboxylic acid groups to methyl ester groups (the "acid:ester ratio") in these co-polymers determines the pH at which the co-polymer is soluble. The acid:ester ratio may be from about 2:1 to about 1:3, e.g. about 1:1 or, preferably, about 1:2. The molecular weight ("MW") of preferred anionic co-polymers is usually from about 120,000 to 150,000, preferably about 125,000 or about 135,000.

Preferred co-polymers for the third polymeric material are discussed in detail in the section above relating to the second polymeric material, and include Eudragit® L; Eudragit® S; Eudragit® FS 30 D; Eudragit® L30D-55; and Eudragit® L100-55.

The exemplary polymers may be used as the third polymeric material in non-neutralised form (provided the pH threshold of the polymer is less than the pH threshold of the second polymeric material—see above) or may be used in at least partially, more preferably fully, neutralised form.

Partially neutralised polymers suitable for use as the third polymeric material, and their methods of production, are known in the art, for example from US2008/0200482A and WO2008/135090A. These polymers may be fully neutralised by the addition of further base to the coating solutions.

In preferred embodiments, the third polymeric material is an at least partially, preferably fully, neutralised co-polymer of (meth)acrylic acid and a (meth)acrylic acid $C_{1-4}$ alkyl ester. In particularly preferred embodiments, the third polymeric material is a fully neutralised co-polymer of (meth)acrylic acid and (meth)acrylic acid methyl ester, particularly Eudragit® S.

The Inventors have observed that fully neutralised Eudragit® S is capable of forming a film and is readily and completely soluble in water independently of at least the range of pH found in the intestine, e.g. about pH 5 to about pH 8. Fully neutralised Eudragit® S is particularly preferred for use as the third polymeric material in the present invention.

Other polymers suitable for use as the third polymeric material include pharmacologically acceptable non-ionic polymers, i.e. pharmacologically acceptable polymers which do not ionise in aqueous media. In these embodiments, the inner layer additionally comprises at least one additive selected from a buffer agent and a base. In particular, the inner layer of these embodiments preferably comprises a base and, optionally, a buffer agent. In preferred embodiments, the inner layer comprises both a buffer agent and a base. Suitable examples of buffer agents and bases are discussed below.

Examples of suitable non-ionic polymers include methylcellulose (MC), hydroxypropyl cellulose (HPC), hydroxypropyl methylcellulose (HPMC), poly(ethylene oxide)-graftpolyvinyl alcohol, polyvinylpyrrolidone (PVP) and polyvinyl alcohol (PVA).

Mixtures of film forming polymer materials may be used as appropriate. The polymer components in such mixtures may be anionic polymers, non-ionic polymers, or a mixture of anionic and non-ionic polymers. An example of a suitable mixture would include a mixture, e.g. a 1:1 mixture, of Eudragit® L and Eudragit® S, and a mixture, e.g. a 1:1 mixture, of Eudragit® S and HPMC. However, the use of a particular film forming polymeric material alone, e.g. a poly(methacrylic acid/methyl methacrylate) co-polymer and Eudragit® S in particular, is preferred.

Base

In preferred embodiments, the inner layer comprises at least one base. The purpose of the base is to provide an alkaline environment on the underside of the outer layer once intestinal fluid begins to penetrate the outer layer. Without being bound by any particular theory, the Inventors believe that the alkaline environment facilitates dissolution of the outer layer and thereby also disintegration of the outer layer since the pH of the alkaline environment is above the pH threshold of the second polymeric material, thereby accelerating release of the drug from the formulation.

In principle, any pharmacologically acceptable base may be used. The base is typically a non-polymeric compound. Suitable bases include inorganic bases such as sodium hydroxide, potassium hydroxide and ammonium hydroxide, and organic bases such as triethanolamine, sodium bicarbonate, potassium carbonate, trisodium phosphate, trisodium citrate or physiologically tolerated amines such as triethylamine. Hydroxide bases in general, and sodium hydroxide in particular, are preferred.

In embodiments in which the third polymeric material is a fully neutralised polycarboxylic acid polymer, the base entrapped within the inner layer is usually the base that was used to neutralise the polymer and to adjust the pH of the inner coating preparation to a pH from about pH 5.5 to about pH 10, e.g. about pH 7.5 to about pH 10 (see below).

In embodiments in which the third polymeric material is a non-ionic polymer, the inner layer usually comprises either a base, or more typically a combination of a base and a buffer agent.

The amount of base present in the inner layer would depend at least in part on the final pH of the inner coating preparation prior to coating a given batch of cores; the number of cores to be coated in the batch; the amount of the inner coating preparation used in the coating process of the batch; and the efficiency of the coating process in terms of the amount of wasted coating preparation.

Buffer Agent

The inner coating preferably comprises at least one buffer agent. The purpose of the buffer agent is to provide or increase pH/buffer capacity on the underside of the outer layer once intestinal fluid begins to penetrate the outer layer. Without wishing to be bound by any particular theory, the Inventors believe that the buffer agent increases the buffer capacity in the dissolving inner layer and assists the ionisation and dissolution of the polymer(s) in the outer layer. It is believed that, for a given pH, the higher the buffer capacity, the faster the rate of polymer dissolution. In embodiments where there is a base in the inner layer, the buffer agent helps maintains the alkaline environment under the outer layer once intestinal fluid penetrates the outer layer.

The buffer agent may be an organic acid such as a pharmacologically acceptable non-polymeric carboxylic acid, e.g. a carboxylic acid having from 1 to 16, preferably 1 to 3, carbon atoms. Suitable carboxylic acids are disclosed in WO2008/135090A. Citric acid is an example of such a carboxylic acid. The carboxylic acids may be used in carboxylate salt form, and mixtures of carboxylic acids, carboxylate salts or both may also be used.

The buffer agent may also be an inorganic salt such as an alkali metal salt, an alkali earth metal salt, an ammonium salt, and a soluble metal salt. As metals for the soluble metal salts, manganese, iron, copper, zinc and molybdenum can be mentioned. Further preferred, the inorganic salt is selected from chloride, fluoride, bromide, iodide, phosphate, nitrate, nitrite, sulphate and borate. Phosphates such as potassium dihydrogen phosphate are preferred over other inorganic buffer salts and organic acid buffers due to their greater buffer capacity at the pH of the coating solution, for example pH 8.

The buffer agent(s) is usually present in the inner layer in an amount from about 0.1 wt % to about 50 wt %. In embodiments in which the soluble (or third) polymeric material is an at least partially neutralised polycarboxylic acid, the buffer agent(s) is usually present in the inner layer in an amount from about 0.1 to about 20 wt %, e.g. from about 0.1 to about 4 wt %, preferably from about 0.1 to about 3 wt %, and more preferably about 1 wt %, based on the dry weight of the third polymeric material. In embodiments in which the soluble (or third) polymeric material is a non-ionic polymer, the buffer agent(s) is usually present in an amount from about 10 wt % to 30 wt %, based on the dry weight of the third polymeric material.

Inner Layer

In addition to the buffer agent and/or the base, the inner layer may comprise conventional excipients for polymer films, including those excipients selected from plasticizers (such a triethyl citrate), anti-tack agents (such as GMS), and surfactants (such as polysorbate 80).

The thickness of the inner coating of the core is typically from about 10 μm to about 150 μm. The inner layer typically has a polymer coating amount from about 2 mg/cm$^2$ to about 10 mg/cm$^2$, preferably from about 2 mg/cm$^2$ to about 8 mg/cm$^2$, and most preferably from about 3 mg/cm$^2$ to about 7 mg/cm$^2$, based on the dry weight of the third polymeric material, particularly for cores having a diameter from about 0.2 mm to about 30 mm.

Optional Additional Layers

The formulation of the present invention may have a top coating layer coating the outer layer. The formulation may also comprise an intermediate layer between the outer and inner layers, provided that the intermediate layer does not affect adversely the release characteristics of the formulation. However, the outer layer is usually provided in contact with the inner layer, that is to say the outer layer is usually applied directly on to the inner layer, i.e. there is usually no intermediate layer separating the inner and outer layers.

The Core

The "core" is the solid body on which the inner layer is applied. The core may be any suitable dosage form, for example, a tablet, a pellet, a granule, a microparticle, a hard or soft capsule, or a microcapsule. In preferred embodiments, the core is a tablet or a capsule.

The invention has application in embodiments in which the core is compatible with the inner layer which is typically alkaline, or provides an alkaline environment on exposure to moisture. Such embodiments are likely to include cases where the core is neutral, or is at neutral pH. However, the invention has particular application in embodiments in which the core or components within the core are incompatible with the inner layer. Such embodiments are likely to include cases where the core is acidic, or is at an acidic pH. Such an acidic core would not be compatible with an alkaline inner layer and the isolation layer would have the added benefit of preventing unwanted interaction between the core and the inner layer.

The core comprises the drug(s). The drug(s) may be contained within the body of the core, for example within the matrix of a tablet or pellet, or within the contents encapsulated within a capsule. Alternatively, the drug may be in a coating applied to the core, for example where the core is a bead of edible material such as sugar, e.g. where the core is in the form of a nonpareil bead or dragée. The core may be "acidic" because the drug or any component within the core comprises at least one acidic group.

The core may consist of the drug(s) alone, or more usually may consist of the drug(s) and at least one pharmacologically acceptable excipient. In this connection, the core is typically a tablet or pellet and consists of a mixture of the drug(s) with a filler or diluent material, e.g. lactose or cellulose material such as microcrystalline cellulose; a binder, e.g. polyvinylpyrrolidone ("PVP") or hydroxypropyl methylcellulose (HPMC); a disintegrant, e.g. croscarmellose sodium (e.g. Ac-Di-Sol™) and sodium starch glycolate (e.g. Explotab™); and/or a lubricant, e.g. magnesium stearate and talc. The core may be a compressed granulate comprising at least some of these materials.

The minimum diameter of each core is typically at least about $10^{-4}$ m, usually at least about $5\times10^{-4}$ m and, preferably, at least about $10^{-3}$ m. The maximum diameter is usually no more than 30 mm, typically no more than 25 mm and, preferably, no more than 20 mm. In preferred embodiments, the core has a diameter from about 0.2 mm to about 25 mm, and preferably from about 0.2 mm to about 4 mm (e.g. for pellets or mini-tablets) or from about 15 mm to about 25 mm (e.g. for certain tablets or capsules). The term "diameter" refers to the largest linear dimension through the core.

The formulation may comprise a plurality of coated cores in order to provide a single dose of the drug(s), particularly in embodiments in which the core is "small", e.g. having a diameter of less than 5 mm. Multiunit dosage forms comprising coated cores having a diameter of less than 3 mm may be preferred.

The present invention has application in a multi-phasic drug release formulation comprising at least two pluralities of coated cores, e.g. coated pellets, in the same dosage form, e.g. a capsule, in which the coated cores of one plurality are differentiated from the coated cores of the or each other plurality by the coating. The coatings may differ from one plurality to the next in terms of coating thickness or composition, e.g. the ratio and/or identity of components. Multiphasic drug release formulations would be particularly suitable for suffers of Crohn's disease affecting different regions along the intestine.

Release from formulations according to the present invention is typically delayed until the proximal small intestine, usually at least the distal ileum and, preferably, the colon. Release from certain formulations may also be sustained. However, in preferred formulations, release is pulsatile.

The time between initial exposure to conditions suitable for drug release and the start of drug release is known as the "lag time". The lag time depends on a number of factors including coating thickness and composition and may vary from one patient to the next. Formulations according to the present invention usually display a lag time in colonic conditions of at least 10 minutes. In most embodiments, the lag time is from about 10 minutes to about 8 hours. For example, the lag time in faecal slurry at pH 6.8 may be from about 10 minutes to about 2 hours, e.g. from about 30 minutes to about 1.5 hours. Complete release of the drug may be achieved in no more than 5 hours, e.g. no more than 4 hours, after exposure to these conditions.

A formulation is usually defined as gastric resistant if there is less than 10 wt % drug release in acidic media after 2 hours. Formulations according to the present invention typically display far less than 10 wt % drug release in acidic media and may be considered to be gastric resistant. The formulations usually display less than 1 wt % drug release in acidic media and, typically, display substantially no drug release in acidic media. When starch is combined with an acrylate film forming material to form the outer layer of the coating for the core, typically less than 5% drug release occurs over 5 hours in conditions simulating the stomach and small intestine.

In one embodiment, the core is a tablet having a diameter of 15-25 mm. The outer layer preferably comprises a 30:70 mixture of high amylose starch, e.g. Eurylon™ VII or VI, and a polymethacrylate polymer, e.g. Eudragit™ S, and the inner layer preferably comprises a fully neutralized polymethacrylate polymer, e.g. Eudragit™ S, applied from an inner coating preparation having a pH of about 8. The core is preferably coated with the inner layer to a thickness from about 3 to about 7 mg/cm$^2$ (based on dry weight of the polymethacrylate polymer) to form an inner layer coated core, which is then coated with the outer layer to a thickness from about 4 to about 8 mg/cm$^2$ (based on dry weight of polymethacrylate polymer).

Different Aspects

Release of a drug in the colon may be considered to be a medical method under a broad definition of the term. However, in the absence of treatment of a particular indication, acceleration of initial drug release in the colon may be viewed as a non-medical technical effect. Accordingly, there is provided, by way of a second aspect of the present invention, a non-medical use of an isolation layer to accelerate drug release in the intestine of a subject from a delayed release drug formulation for oral administration to said subject, said formulation comprising:

a core comprising said drug;
said isolation layer coating said core; and
an outer coating for providing intestinal release of said drug, said outer coating comprising an outer layer and an inner layer, wherein the outer layer comprises a pH dependently soluble polymeric material which has a pH threshold at about pH 5 or above, and wherein the inner layer comprises a soluble polymeric material which is soluble in intestinal fluid or gastrointestinal fluid, said soluble polymeric material being selected from the group consisting of a polycarboxylic acid polymer that is at least partially neutralised, and a non-ionic polymer, provided that, where said soluble polymeric material is a non-ionic polymer, said inner layer comprises at least one additive selected from a buffer agent and a base.

According to a third aspect of the present invention, there is provided a method of accelerating drug release in the colon of a subject from a delayed release drug formulation for oral administration to said subject, said formulation comprising:

a core comprising said drug; and
an outer coating for providing intestinal release of said drug, said outer coating comprising an outer layer and an inner layer, wherein the outer layer comprises a pH dependently soluble polymeric material which has a pH threshold at about pH 5 or above, and wherein the inner layer comprises a soluble polymeric material which is soluble in intestinal fluid or gastrointestinal fluid, said soluble polymeric material being selected from the group consisting of a polycarboxylic acid polymer that is at least partially neutralised, and a non-ionic polymer, provided that, where said soluble polymeric material is a non-ionic polymer, said inner layer comprises at least one additive selected from a buffer agent and a base, said method comprising providing an isolation layer between said core and said outer coating.

According to a fourth aspect of the present invention, there is provided a method of producing a delayed release drug formulation for oral administration, wherein said formulation provides accelerated release of a drug in the intestine of a subject, said method comprising:

providing a core comprising said drug;
coating said core with an isolation layer to produce an isolation layer coated core; and
coating said isolation layer coated core with an outer coating for providing intestinal release of said drug, said outer coating comprising an outer layer and an inner layer, wherein the outer layer comprises a pH dependently soluble polymeric material which has a pH threshold at about pH 5 or above, and wherein the inner layer comprises a soluble polymeric material which is soluble in intestinal fluid or gastrointestinal fluid, said soluble polymeric material being selected from the group consisting of a polycarboxylic acid polymer that is at least partially neutralised, and a non-ionic polymer, provided that, where said soluble polymeric material is a non-ionic polymer, said inner layer comprises at least one additive selected from a buffer agent and a base, The Inventors have developed some new formulations that are not disclosed in the art and which demonstrate unexpected acceleration of initial drug release after exposure to the typical pH conditions of the colon. The formulations in question use the pH dependently soluble (or second) polymeric material as the sole film-forming material in the outer layer. Thus, according to a fifth aspect of the present invention, there is provided a delayed release drug formulation for oral administration to deliver a drug to the intestine of a subject, said formulation comprising:

a core comprising said drug;
said isolation layer coating said core; and
an outer coating for providing intestinal release of said drug, said outer coating comprising an outer layer and an inner layer,
wherein the outer layer comprises a film-forming polymeric material consisting of a pH dependently soluble polymeric material which has a pH threshold at about pH 5 or above,
wherein the inner layer comprises a soluble polymeric material which is soluble in intestinal fluid or gastrointestinal fluid, said soluble polymeric material being selected from the group consisting of a polycarboxylic acid polymer that is at least partially neutralised, and a non-ionic polymer, provided that, where said soluble polymeric material is a non-ionic polymer, said inner layer comprises at least one additive selected from a buffer agent and a base. Release of the drug in the colon from these formulations is typically accelerated as described above.

In addition, according to a sixth aspect of the present invention, there is provided a delayed release drug formulation for oral administration to deliver a drug to the intestine of a subject, said formulation comprising:
a core comprising said drug;
said isolation layer coating said core; and
an outer coating for providing intestinal release of said drug, said outer coating comprising an outer layer and an inner layer,
wherein the outer layer comprises a pH dependently soluble polymeric material which has a pH threshold at about pH 5 or above,
wherein the inner layer comprises a soluble polymeric material which is soluble in intestinal fluid or gastrointestinal fluid, said soluble polymeric material being selected from the group consisting of a polycarboxylic acid polymer that is at least partially neutralised, and a non-ionic polymer, provided that, where said soluble polymeric material is a non-ionic polymer, said inner layer comprises at least one additive selected from a buffer agent and a base, and
wherein release of said drug in the intestine is accelerated.

As described above, the Inventors have discovered that the use of an isolation layer also improves the stability of the formulation during storage. In this regard, according to a seventh aspect of the present invention, there is provided use of an isolation layer to prevent deceleration of drug release in the intestine of a subject from a delayed release drug formulation for oral administration to said subject after storage, said formulation comprising:
a core comprising said drug;
said isolation layer coating said core; and
an outer coating for providing intestinal release of said drug, said outer coating comprising an outer layer and an inner layer,
wherein the outer layer comprises a pH dependently soluble polymeric material which has a pH threshold at about pH 5 or above, and
wherein the inner layer comprises a soluble polymeric material which is soluble in intestinal fluid or gastrointestinal fluid, said soluble polymeric material being selected from the group consisting of a polycarboxylic acid polymer that is at least partially neutralised, and a non-ionic polymer, provided that, where said soluble polymeric material is a non-ionic polymer, said inner layer comprises at least one additive selected from a buffer agent and a base.

For colonic release formulations, lag time ($T_{lag}$) in vitro in Krebs buffer at pH 7.4 after 2 h at 0.1M HCl is typically increased after storage by no more than 5%. In absolute terms, lag time ($T_{lag}$) in vitro in Krebs buffer at pH 7.4 after 2 h at 0.1M HCl is typically increased after storage by no more than 10 minutes and preferably by no more than 5 minutes.

The effect typically results after storage in closed high density polyethylene (HDPE) containers for at least 1 month at 40° C./75% RH and/or after storage in closed HDPE containers for at least 3 months at 25° C./60% RH, and is particularly significant when the isolation layer comprises HPMC. Additionally or alternatively, the outer layer preferably comprises the pH dependently soluble polymeric material in admixture with a digestible polymeric material susceptible to attack by colonic bacteria.

In the second to seventh aspects of the present invention, the formulation may be as defined in any of the embodiments defined in respect of the first aspect.

According to a further aspect of the present invention, there is provided a formulation according any previous aspect for use in a method of medical treatment of the human or animal body by therapy.

The core comprises at least one drug. The formulation is usually used to administer a single drug as the sole therapeutically active component. However, more than one drug may be administered in a single formulation.

The formulation of the present invention is designed to administer a wide range of drugs. Suitable drugs include those drugs which are known for intestinal administration using known delayed release oral formulations. The present invention may be used to administer drugs having a local or a systemic effect.

The formulation of the present invention has particular application in the intestinal administration of a drug comprising at least one acidic group such as a carboxylic acid group. Such drugs may be acidic drugs or zwitterionic drugs. An example of such a drug is 5-aminosalicylic acid (5ASA or mesalazine).

The identity of the drug(s) in the formulation obviously depends on the condition to be treated. In this connection, the formulation has particular application in the treatment of IBD (including Crohn's disease and ulcerative colitis); IBS; constipation; diarrhoea; infection; and carcinoma, particularly colon or colorectal cancer.

For the treatment or prevention of IBD, the formulation may comprise at least one drug selected from the group consisting of anti-inflammatory agents (e.g. 5ASA (otherwise known as mesalazine or mesalamine), 4ASA, sulphasalazine and balsalazide); non-steroidal anti-inflammatory agents (e.g. ibuprofen and diclofenac); steroids (e.g. prednisolone; budesonide or fluticasone); immunosuppressants (e.g. azathioprine; cyclosporin; and methotrexate); antibiotics; and biological agents including peptides, proteins and antibody fragments. Suitable examples of biological agents include alkaline phosphatase and anti-TNF antibodies such as infliximab, adalimumab, certulizumab pegol, golimumab and ustekinumab.

For the treatment or prevention of cancer, the formulation may comprise at least one antineoplastic agent. Suitable antineoplastic agents include fluorouracil; methotrexate; dactinomycin; bleomycin; etoposide; taxol; vincristine; doxorubicin; cisplatin; daunorubicin; VP-16; raltitrexed; oxaliplatin; and pharmacologically acceptable derivatives and salts thereof. For the prevention of colon cancer or colorectal cancer, primarily in patients suffering from colitis, the formulation may comprise the anti-inflammatory agent, 5ASA.

For the treatment or prevention of IBS, constipation, diarrhoea or infection, the formulation may comprise at least one active agent suitable for the treatment or prevention of these conditions.

Pharmacologically acceptable derivatives and/or salts of the drugs may also be used in the formulation. An example of a suitable salt of prednisolone is methyl prednisolone sodium succinate. A further example is fluticasone propionate.

The present invention has particular application in either the treatment of IBD (particularly, ulcerative colitis) or the prevention of colon cancer or colorectal cancer (primarily in colitis patients), both using 5ASA. It also has application as a portal of entry of drugs into the systemic circulation via the colon. This is particularly advantageous for peptide and protein drugs which are unstable in the upper gastrointestinal tract. The present invention may also be utilised for the purpose of chronotherapy.

In another aspect of the invention, there is provided a method of targeting a drug to the colon comprising administering to a patient a formulation as defined above.

In a yet further aspect of the invention, there is provided the use of a formulation as defined above in the manufacture of a medicament for the treatment or prevention of IBD (particularly ulcerative colitis); IBS; constipation; diarrhoea; infection; and cancer.

There is also provided the use of at least one drug selected from anti-inflammatory agents and steroids in the manufacture of a medicament comprising a formulation as defined above for use in the treatment of IBD. In addition, there is also provided the use of at least one antineoplastic agent in the manufacture of a medicament comprising a formulation as defined above for use in the treatment of carcinoma. Further, there is also provided use of 5ASA in the manufacture of a medicament comprising a formulation as defined above for use in the prevention of colon cancer or colorectal cancer.

According to a still further aspect of the present invention, there is provided a method of medical treatment or prevention of IBD or carcinoma comprises administering to a patient a therapeutic amount of a formulation as defined above.

The formulation will typically comprise a therapeutically effective amount of the or each drug which may be from about 0.01 wt % to about 99 wt %, based on the total weight of the formulation. The actual dosage would be determined by the skilled person using his common general knowledge. However, by way of example, "low" dose formulations typically comprise no more than about 20 wt % of the drug, and preferably comprise from about 1 wt % to about 10 wt %, e.g. about 5 wt %, of the drug. "High" dose formulations typically comprise at least 40 wt % of the drug, and preferably from about 45 wt % to about 85 wt %, e.g. about 50 wt % or about 80 wt %.

Method

In preferred embodiments, the method of producing a delayed release drug formulation for oral administration to deliver a drug to the colon typically comprises:
  forming a core comprising a drug;
  coating the core with an isolation layer to form an isolated core;
  coating the isolated core using an inner coating preparation comprising the soluble (or third) polymeric material as defined above, in a solvent system to form an inner coated core;
  coating the inner coated core with an outer coating preparation comprising a pH dependently soluble (or second) polymeric material which has a pH threshold of about pH 5 or above in a solvent system, to form an outer coated core,
wherein, where the soluble (or third) polymeric material is a non-ionic polymer, the inner coating preparation comprises at least one additive selected from the group consisting of a buffer agent and a base.

The outer coating layer preparation preferably includes a digestible (or first) polymeric material and the solvent system of the inner coating preparation is preferably aqueous.

In embodiments where the third polymeric material is an at least partially neutralised polycarboxylic acid polymer, said method typically comprises dispersing a polycarboxylic acid polymer in a solvent, optionally with a buffer agent, and adding base to at least partially neutralise the polycarboxylic acid polymer to form the inner coating preparation. In preferred embodiments, the amount of base added is at least sufficient to fully neutralise the polycarboxylic acid polymer.

In embodiments where the third polymeric material is a non-ionic polymer, the pH of the inner coating preparation is preferably adjusted prior to coating to be at least 0.5 pH units higher than the pH threshold of the second polymeric material.

The pH of the inner coating preparation is preferably adjusted to be from about pH 5.5 to about pH 10, e.g. from about pH 7.5 to about pH 8.5, preferably from about pH 7.8 to about pH 8.2, and more preferably about pH 8.

The outer coating may be applied using the method described in WO2007/122374A.

EXAMPLES

Preferred embodiments of the present invention will now be described with reference to the drawings, in which:—

FIG. 1 is a graph comparing drug release in 0.1N HCl (2 hours) followed by Krebs buffer pH 7.4 as a function of time, from 400 mg 5ASA tablets, coated with (a) an isolation layer of HPMC, an inner layer of neutralized Eudragit S and an outer layer of Eudragit® S (Example 1), (b) coated with an inner layer of neutralized Eudragit S and an outer layer of Eudragit® S (Comparative Example 1) and (c) coated with a single layer of Eudragit S (Comparative Example 2);

Figure 4:
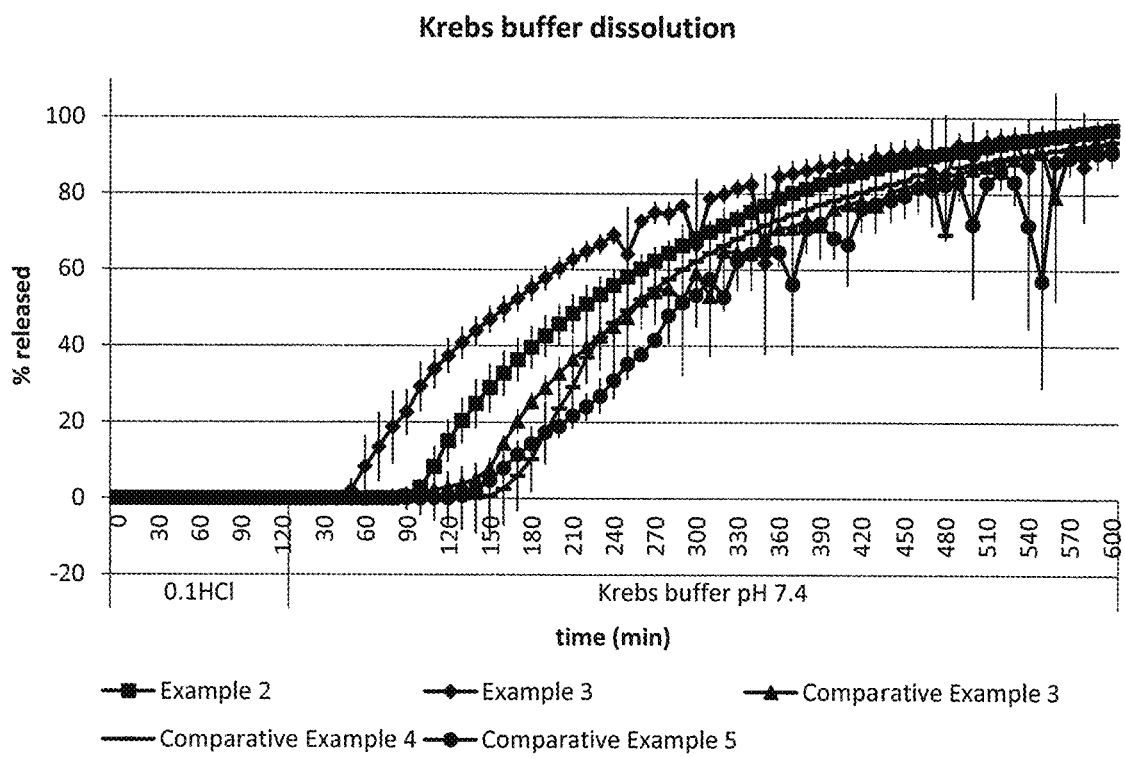
Figure 5:
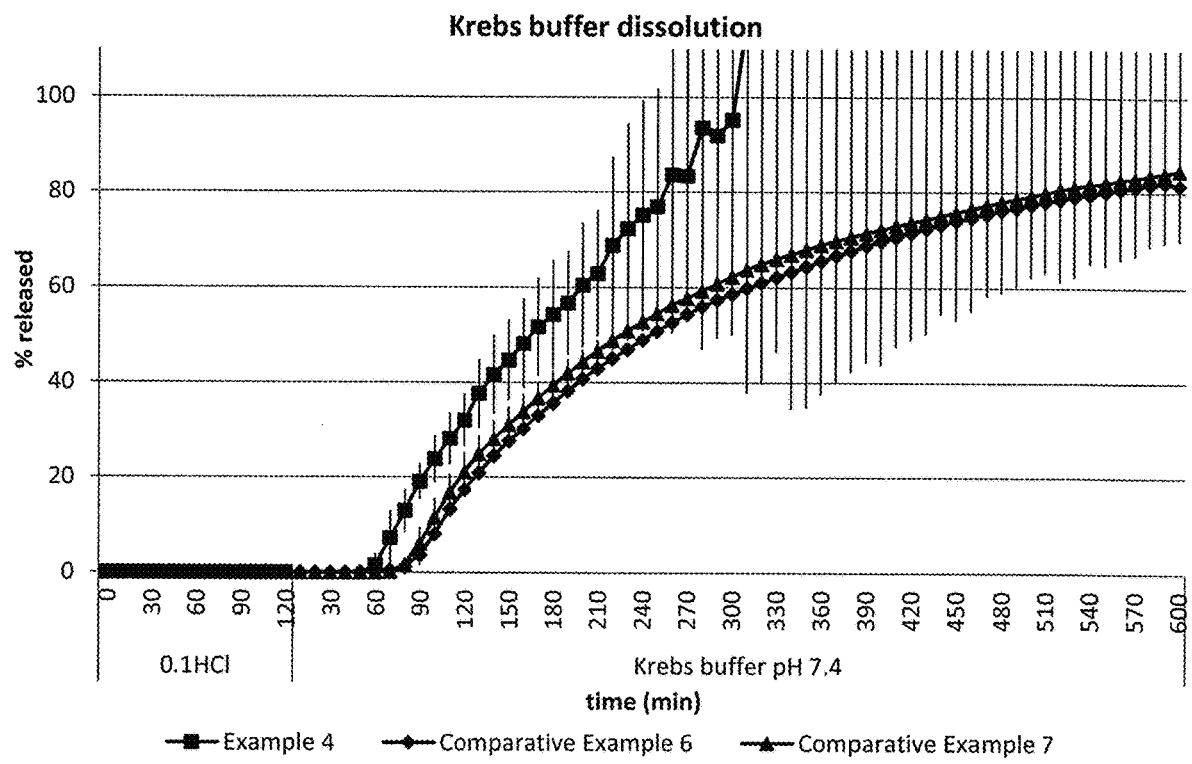
Figure 6:
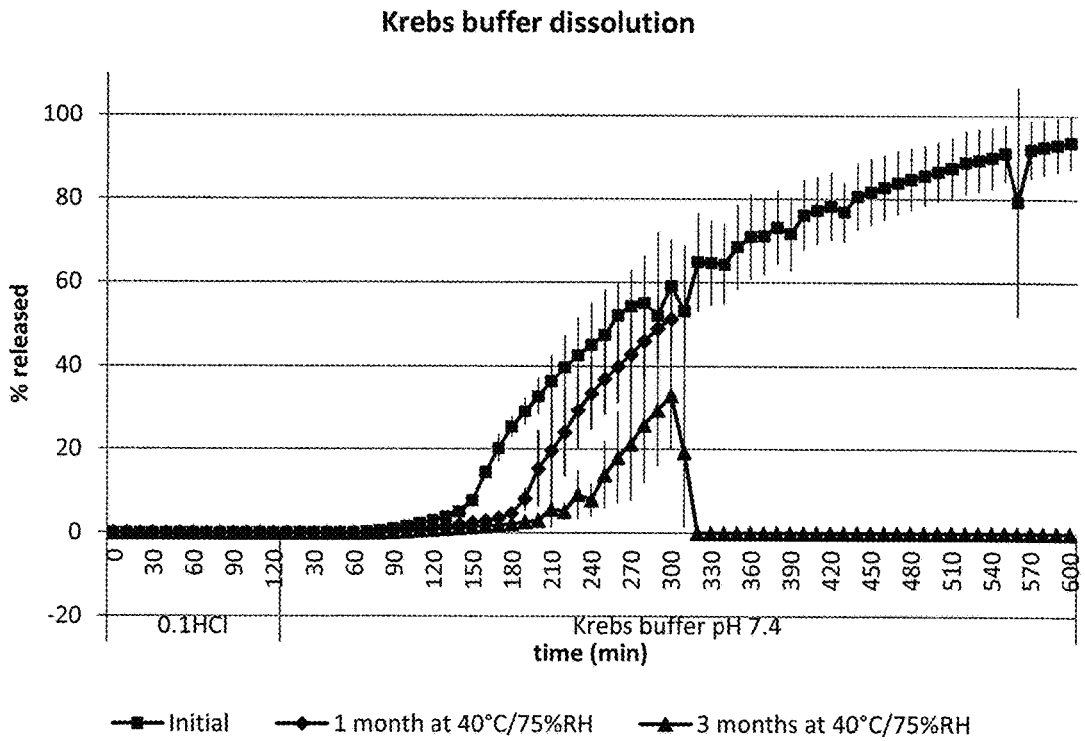
Figure 7:
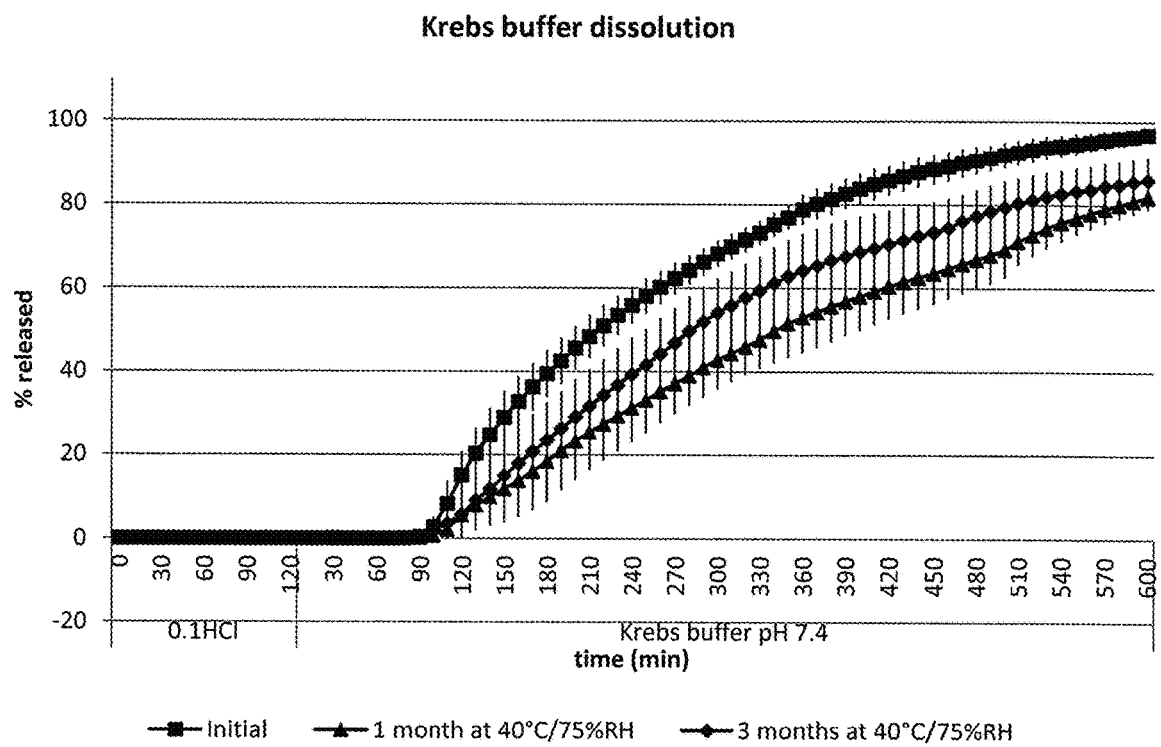
Figure 8:
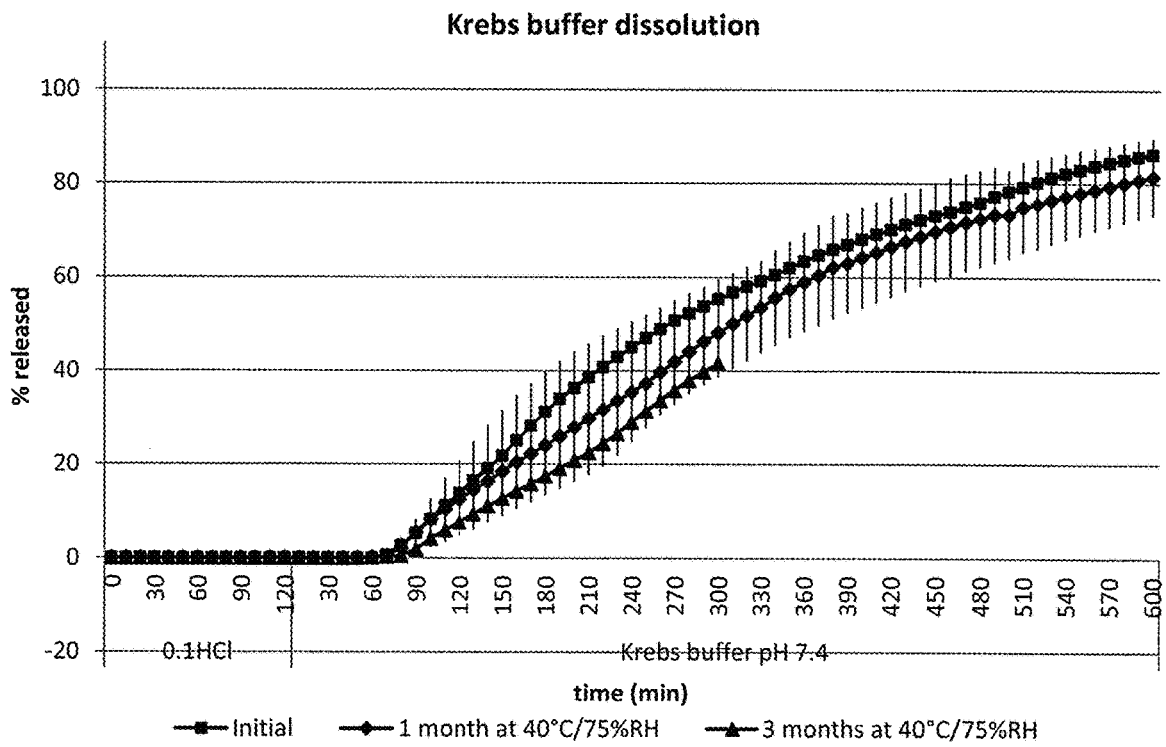
Figure 9:
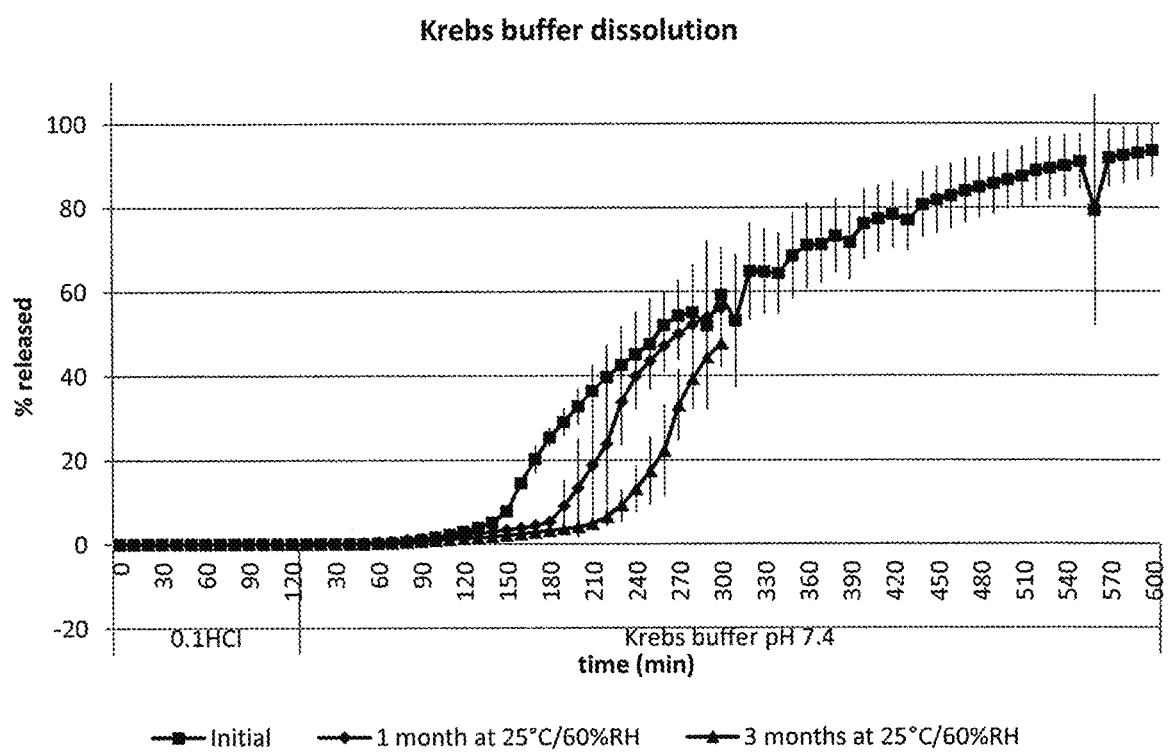
Figure 10:
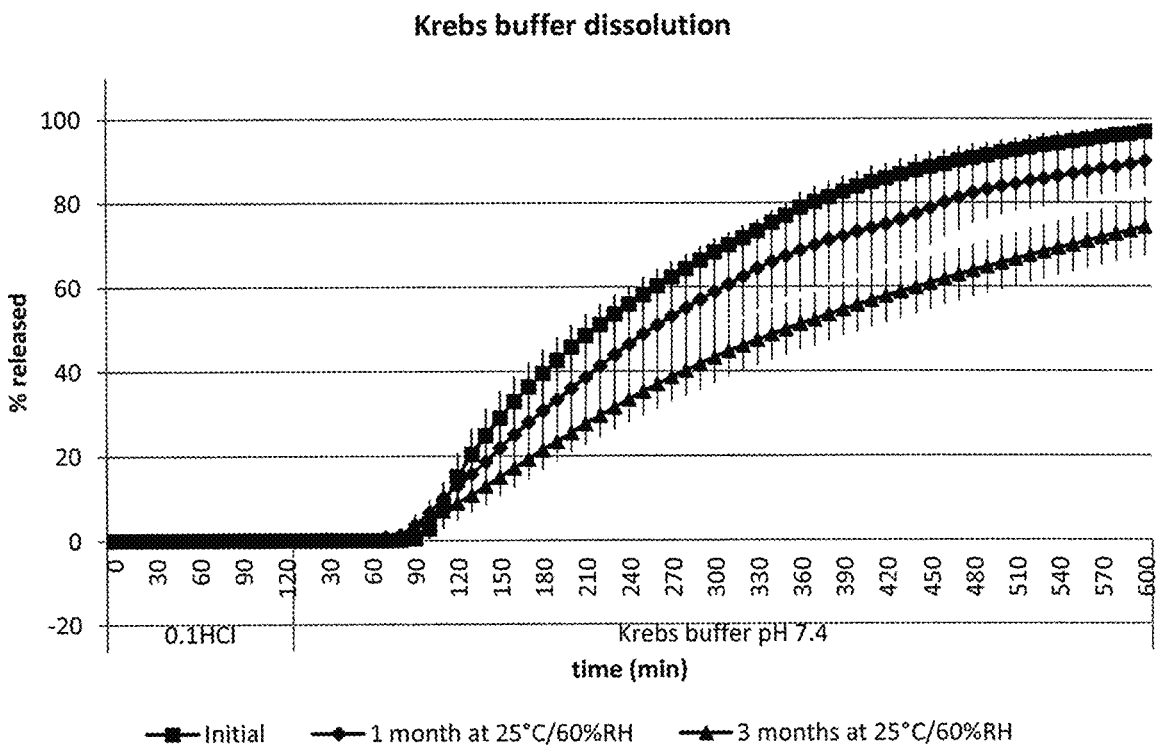
Figure 11:
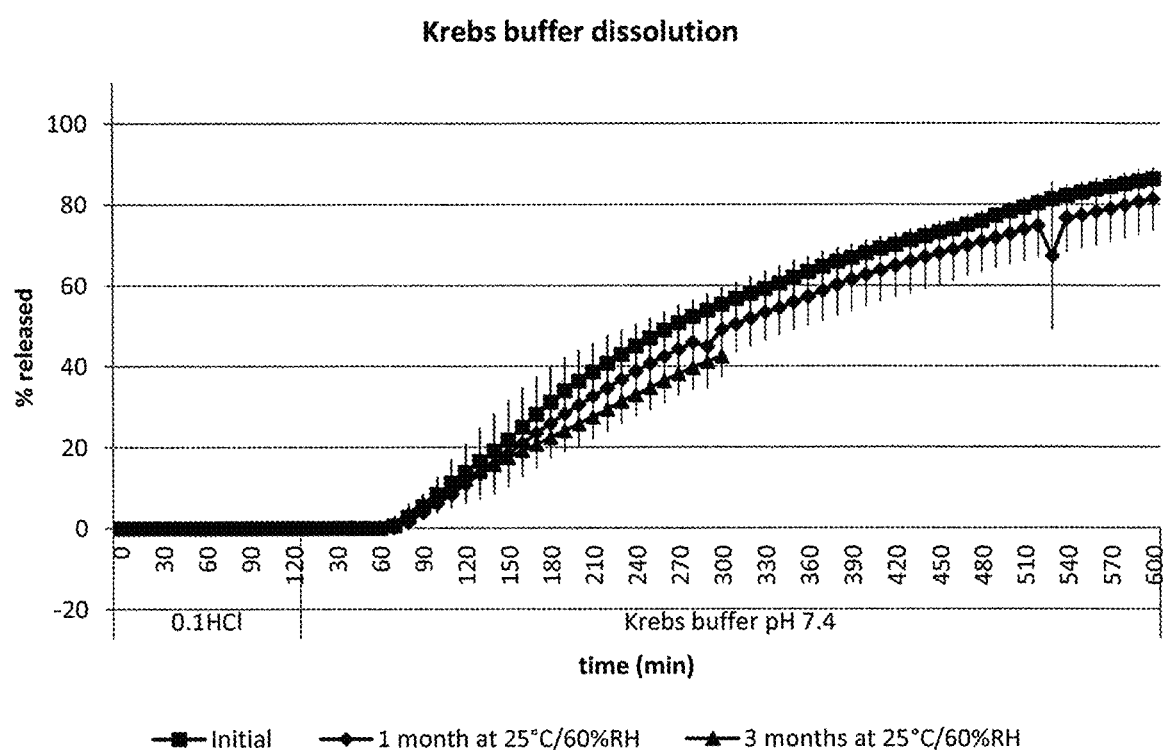

FIG. 4 is a graph comparing drug release in 0.1N HCl (2 h) followed by Krebs buffer pH 7.4 as a function of time from 800 mg 5ASA tablets coated with (a) an isolation layer of HPMC, an inner layer of neutralized Eudragit® S and an outer layer of 30:70 mixture of starch:Eudragit® S (Example 2), (b) an isolation layer of PVA (Opadry AMB), an inner layer of neutralized Eudragit® S and an outer layer of 30:70 mixture of starch:Eudragit® S (Example 3), (c) an inner layer of neutralized Eudragit® S and an outer layer of 30:70 mixture of starch:Eudragit® S (Comparative Example 3), (d) an isolation layer of HPMC and an outer layer of 30:70 mixture of starch:Eudragit® S (Comparative Example 4), (e) an outer layer of 30:70 mixture of starch:Eudragit® S (Comparative Example 5);

FIG. 5 is a graph comparing drug release in 0.1N HCl (2 h) followed by Krebs buffer pH 7.4 as a function of time from 1200 mg 5ASA tablets coated with an isolation layer of HPMC, an inner layer of neutralized Eudragit® S and an outer layer of 30:70 mixture of starch:Eudragit® S, wherein the isolation layer has a thickness of (a) 1 mg/cm$^2$ (Comparative Example 6) (b) 3 mg/cm$^2$ (Example 4), or (c) 5 mg/cm$^2$ (Comparative Example 7);

FIG. 6 is a graph comparing drug release in 0.1N HCl (2 h) followed by Krebs buffer pH 7.4 as a function of time from 800 mg 5ASA tablets coated with an inner layer of neutralized Eudragit® S and an outer layer of 30:70 mixture of starch:Eudragit® S (Comparative Example 3) before storage (Initial) and after storage in a closed HDPE bottle at 40° C./75% RH for 1 month and 3 months;

FIG. 7 is a graph comparing drug release in 0.1N HCl (2 h) followed by Krebs buffer pH 7.4 as a function of time from 800 mg 5ASA tablets coated with an isolation layer of HPMC, an inner layer of neutralized Eudragit® S and an outer layer of 30:70 mixture of starch:Eudragit® S (Example 2) before storage (Initial) and after storage in a closed HDPE bottle at 40° C./75% RH for 1 month and 3 months;

FIG. 8 is a graph comparing drug release in 0.1N HCl (2 h) followed by Krebs buffer pH 7.4 as a function of time from 800 mg 5ASA tablets coated with an isolation layer of HPMC, an inner layer of neutralized Eudragit® S and an outer layer of 50:50 mixture of starch:Eudragit® S (Example 5) before storage (Initial) and after storage in a closed HDPE bottle at 40° C./75% RH for 1 month and 3 months;

FIG. 9 is a graph depicting drug release in 0.1N HCl (2 h) followed by Krebs buffer pH 7.4 as a function of time from 800 mg 5ASA tablets coated with an inner layer of neutralized Eudragit® S and an outer layer of 30:70 mixture of starch:Eudragit® S (Comparative Example 3) before storage (Initial) and after storage in an open HDPE bottle at 25° C./60% RH for 1 month and for 3 months;

FIG. 10 is a graph depicting drug release in 0.1N HCl (2 h) followed by Krebs buffer pH 7.4 as a function of time from 800 mg 5ASA tablets coated with an isolation layer of HPMC, an inner layer of neutralized Eudragit® S and an outer layer of 30:70 mixture of starch:Eudragit® S (Example 2) before storage (Initial) and after storage in an open HDPE bottle at 25° C./60% RH for 1 month and 3 months;

FIG. 11 is a graph comparing drug release in 0.1N HCl (2 h) followed by Krebs buffer pH 7.4 as a function of time from 800 mg 5ASA tablets coated with an isolation layer of HPMC, an inner layer of neutralized Eudragit® S and an outer layer of 50:50 mixture of starch:Eudragit® S (Example 5) before storage (Initial) and after storage in an open HDPE bottle at 25° C./60% RH for 1 month and 3 months.

MATERIALS 5-aminosalicylic acid (mesalazine EP) was purchased from Cambrex Karlskoga AB, Karlskoga, Sweden. Lactose (Tablettose 80) was purchased from Meggle, Hamburg, Germany. Sodium starch glycolate (Explotab™) was purchased from JRS Pharma, Rosenberg, Germany. Talc was purchased from Luzenac Deutschland GmbH, Dusseldorf, Germany. Polyvinylpyrrolidone (PVP) was purchased from ISP Global Technologies, Köln, Germany. Magnesium stearate was purchased from Peter Greven GmbH, Bad Münstereifel, Germany. Eudragit® S 100, Eudragit® L 30 D-55 and Eudragit® FS 30 D were all purchased from Evonik GmbH, Darmstadt, Germany. Maize starch (NI-460 and Eurylon VI or 6) was purchased from Roquette, Lestrem, France. Polysorbate 80, butan-1-ol and sodium hydroxide were all purchased from Sigma-Aldrich, Buchs, Switzerland. Potassium dihydrogen phosphate, glyceryl monostearate (GMS), triethyl citrate (TEC) and ammonia solution (25%) were all purchased from VWR International LTD, Poole, UK.

Preparation of 400 mg 5ASA Tablet Cores

Oblong shaped 400 mg 5ASA tablet cores with dimensions 14.5×5.7 mm were prepared by fluid bed granulation followed by blending and compression. Each tablet contained 76.9 wt % 5ASA (400 mg; drug); 14.7 wt % lactose (filler); 1.7 wt % PVP (binder); 3.5 wt % sodium starch glycolate (disintegrant); and 2 wt % talc and 1.2 wt % magnesium stearate (lubricants).

The obtained tablet cores were coated as discussed below in Examples 1 & 2 and in Comparative Examples 1 to 5.

Preparation of 800 mg 5ASA Tablet Cores

Oblong shaped 800 mg tablets with dimensions 8×17 mm were prepared by granulation followed by blending and compression. Each tablet contained 800 mg 5ASA (drug) and additional excipients, including lactose (filler); PVP (binder); sodium starch glycolate (disintegrant); and talc and magnesium stearate (lubricants).

The obtained tablet cores were coated as discussed below in Examples 8 to 11 and in Comparative Examples 7 to 11.

Preparation of 1200 mg 5ASA Tablet Cores

Oblong-shaped 1200 mg 5ASA tablet cores (having dimensions 21×10 mm) were prepared by wet granulation. Each tablet contained 85.7 wt % 5ASA (1200 mg), 9.2 wt % microcrystalline cellulose, 1.7 wt % HPMC, 2.9 wt % sodium starch glycolate, and 0.5 wt % magnesium stearate.

The obtained tablet cores were coated as discussed below in Examples 3 to 7 and in Comparative Example 6.

Example 1

(400 mg 5ASA tablets with isolation layer of HPMC/inner layer of neutralised Eudragit® S/outer layer of Eudragit® S)

Isolation Layer

The isolation layer was formed from a mixture of HPMC and 10% triethyl citrate (TEC), based on dry polymer weight.

The HPMC was dissolved in water under magnetic stirring and then TEC was added to form a coating preparation. The coating preparation was sprayed onto 400 mg 5ASA cores using a fluid bed spray coating machine to achieve a coating amount of 3 mg polymer/cm$^2$.

The coating parameters were as follows: spray rate 3.1 g/min/kg tablet cores, atomizing pressure 0.2 bar, and inlet air temperature 40° C.

Inner Layer

The inner layer was applied to the isolation layer coated tablets from an aqueous preparation of Eudragit® S 100, where the pH was adjusted to pH 8. The composition of the inner layer also included 50% of triethyl citrate (based on dry polymer weight), 10% potassium dihydrogen phosphate (based on dry polymer weight), 10% glyceryl monostearate (based on dry polymer weight) and 40% polysorbate 80 (based on GMS weight). The pH was adjusted using 1M NaOH until the pH 8 was obtained.

Potassium dihydrogen phosphate and triethyl citrate were dissolved in distilled water, after which a dispersion of Eudragit® S 100 was added under mechanical agitation. The pH was then adjusted to pH 8 with 1M NaOH and the solution was left mixing for 1 hour.

A GMS emulsion was prepared at a concentration of 10% w/w. Polysorbate 80 (40% based on GMS weight) was dissolved in distilled water followed by dispersion of GMS. This preparation was then heated to 75° C. for 15 minutes under strong magnetic stirring in order to form the emulsion. The emulsion was cooled to room temperature under stirring.

The GMS emulsion was added to the neutralised Eudragit® S solution to form an inner layer coating preparation which was coated onto the isolation layer coated tablets using a fluid bed spray coating machine until the coating amount reached 5 mg polymer/cm$^2$ to form inner layer coated tablets.

The coating parameters were as follows: spraying rate 20 ml/min/kg tablets, atomizing pressure 0.2 bar and inlet air temperature 40° C.

Outer Layer

The outer coating layer was applied from an organic solution of Eudragit® S 100. The coating solution contains 20% triethyl citrate (based on dry polymer weight), 10% glyceryl monostearate (based on dry polymer weight) and 40% polysorbate 80 (based on GMS weight).

Triethyl citrate was dissolved in 96% ethanol followed by Eudragit® S 100 under mechanical stirring and mixing was continued for 1 hour.

A GMS emulsion was prepared at a concentration of 10% w/w. Polysorbate 80 (40% based on GMS weight) was dissolved in distilled water followed by dispersion of the GMS. This dispersion was then heated to 75° C. for 15 minutes under strong magnetic stirring in order to form the emulsion. The emulsion was cooled to room temperature under stirring.

The GMS preparation was added to the Eudragit® S 100 solution and the final coating solution was coated on to the inner layer coated tablets using a fluid bed spray coating machine to achieve a coating amount of 5 mg Eudragit® S polymer/cm$^2$.

The coating parameters were as follows: spraying rate 16 ml/min/kg tablets, atomizing pressure 0.2 bar and inlet air temperature 40° C.

Example 2

(800 mg 5ASA tablets with isolation layer of HPMC/inner layer of neutralised Eudragit® S/outer layer of 30:70 mixture of starch:Eudragit® S)

Isolation Layer

The isolation layer was formed from a mixture of HPMC and 20% PEG 6000 (based on dry polymer weight).

The polymer was dissolved in water under magnetic stirring and then the PEG 6000 was added. The final preparation was sprayed onto 800 mg 5ASA cores using a perforated pan coater to achieve a coating amount of 3 mg polymer/cm$^2$ to form isolation layer coated tablets. The coating parameters were as follows: spray rate 2.4 g/min/kg tablet cores, atomizing pressure 0.7 bar, and inlet air volume 15 m$^3$/h/Kg tablets and product temperature 34° C.

Inner Layer

The inner layer was applied using an aqueous preparation of Eudragit® S 100, where the pH was adjusted to pH 8. The composition of the middle layer also includes 70% triethyl citrate (based on dry polymer weight), 1% potassium dihydrogen phosphate (based on dry polymer weight), 10% glyceryl monostearate (based on dry polymer weight) and 40% polysorbate 80 (based on GMS weight). The pH was adjusted using 1M NaOH until the pH 8 is obtained.

Potassium dihydrogen phosphate and triethyl citrate were dissolved in distilled water, followed by dispersion of the Eudragit® S 100 under mechanical agitation. The pH was then adjusted to pH 8 with 1M NaOH and left mixing for 1 h.

A GMS emulsion was prepared at a concentration of 10% w/w. Polysorbate 80 (40% based on GMS weight) was dissolved in distilled water followed by dispersion of GMS. This preparation was then heated to 75° C. for 15 minutes under strong magnetic stirring in order to form an emulsion. The emulsion was cooled to room temperature under stirring.

The GMS emulsion was added to the neutralised Eudragit® S solution and the final preparation was coated onto isolation layer coated tablets using a perforated pan coater until the coating amount reached 5 mg polymer/cm$^2$ to produce inner layer coated tablets. The total solids content of the coating solution was 10%. The coating parameters were as follows: spraying rate 3.1 g/min/kg tablets, atomizing pressure 0.6 bar, inlet air volume 15 m3/h/Kg tablets and product temperature 26.5° C.

Outer Layer

The outer layer was applied using a mixture of an aqueous starch dispersion and an organic Eudragit® S 100 solution. The aqueous starch dispersion was prepared by dispersing maize starch into butan-1-ol, followed by water, under magnetic stirring. The ratio of maize starch:butan-1-ol:water was 1:2:22. The resulting dispersion was heated to boiling and then cooled under stirring overnight. The organic Eudragit® S 100 solution was prepared by dissolving Eudragit® S 100 in 96% ethanol under high speed stirring. The final solution contained about 6% polymer solids.

The starch dispersion was added dropwise to the Eudragit® S 100 solution to obtain a ratio of starch:Eudragit® S of 30:70. The mixture was mixed for 2 h, 20% triethyl citrate (based on total polymer weight) and 5% glyceryl monostearate (GMS, based on total polymer weight) were added and mixing was continued for a further 2 h.

13.18% iron oxide red (based on Eudragit® polymer weight) and 2.27% iron oxide yellow (based on Eudragit® polymer weight) were suspended in ethanol under high shear homogenization and this suspension was added into the starch and Eudragit® mixture and mixed for a further 30 minutes.

The GMS was added in the form of an emulsion prepared at a concentration of 5% w/w. Polysorbate 80 (40% based on GMS weight) was dissolved in distilled water followed by dispersion of the GMS. This dispersion was then heated to 75° C. for 15 minutes under strong magnetic stirring in order to form an emulsion. The emulsion was cooled to room temperature under stirring.

The final preparation was coated onto the inner layer coated tablets using a perforated pan coater machine until a coating having 5 mg Eudragit® polymer/cm$^2$ was obtained. The spray coating parameters were as follows: spraying rate 8.0 g/min/kg tablets, atomizing pressure 0.4 bar, inlet air volume 100 m$^3$/h/Kg tablets and product temperature 34.5° C.

Example 3

(800 mg 5ASA tablets with isolation layer of PVA/inner layer of neutralised Eudragit® S/outer layer of a 30:70 mixture of starch/Eudragit® S)

Isolation Layer

The isolation layer was formed using Opadry® AMB (a polyvinyl alcohol-based product).

The polymer was dissolved in water under magnetic stirring and mixed for 45 minutes. The final preparation was sprayed onto 800 mg 5ASA cores using a pan-coating machine to achieve a coating amount of 3.61 mg Opadry®/cm². The coating parameters were as follows: spray rate 7.0 g/min/kg tablet cores, atomizing pressure 0.6 bar, inlet air volume 75 m³/h per kg tablet cores and product temperature 42° C.

Inner Layer

The inner layer was prepared according to Example 2.

Outer Layer

The outer layer was prepared according to Example 2

Example 4

(1200 mg 5ASA tablets with isolation layer of HPMC (3 mg/cm²)/inner layer of neutralised Eudragit® S/outer layer of 30:70 mixture of starch:Eudragit® S)

Isolation Layer

The isolation layer was prepared according to Example 2. The final preparation was sprayed onto 1200 mg 5ASA cores using a perforated pan-coating machine to achieve a coating amount of 3 mg polymer/cm² to form isolation layer coated tablets. The coating parameters were as follows: spray rate 2.33 g/min. per kg tablet cores, atomizing pressure 0.7 bar, inlet air volume 16.3 m³/h per kg tablet cores and product temperature 33° C.

Inner Layer

The inner coating was prepared according to Example 2. The final preparation was coated on to the isolation layer coated tablets using a perforated pan coater machine until the coating amount reached 5 mg polymer/cm². The total solids content of the coating solution is approximately 10%.

The coating parameters were as follows: spraying rate 2.9 g/min/kg tablets, atomizing pressure 0.6 bar, and inlet air volume 16.3 m³/h/kg tablets and product temperature 33° C.

Outer Layer

The outer layer was prepared according to Example 2. The final preparation was coated onto inner layer coated tablets using a perforated pan coater machine until a coating having 5 mg Eudragit® S polymer/cm² was obtained. The spray coating parameters were as follows: spraying rate 3.1 g/min/kg tablets, atomizing pressure 0.4 bar, inlet air volume 21.7 m³/h/kg tablets and product temperature 34° C.

Example 5

(800 mg 5ASA tablets with isolation layer of HPMC/inner layer of neutralised Eudragit® S/outer layer of a 50:50 mixture of starch/Eudragit® S)

Isolation Layer

The isolation layer was prepared according to Example 2.

Inner Layer

The inner layer was prepared according to Example 2

Outer Layer

The outer layer was applied from a mixture of an aqueous starch dispersion and an organic Eudragit® S 100 solution.

The aqueous starch dispersion was prepared by dispersing maize starch into butan-1-ol, followed by water, under magnetic stirring. The ratio of maize starch:butan-1-ol:water was 1:1:9.53. The resulting dispersion was heated to boiling and then cooled under stirring overnight. The % solids content of the cooled preparation was calculated based on the final weight of the dispersion (considering the evaporation during heating).

The organic Eudragit® S 100 solution was prepared by dissolving Eudragit® S 100 in 96% ethanol under high speed stirring. The final solution contained about 6% polymer solids.

The starch dispersion was added dropwise to the Eudragit® S 100 solution to obtain a ratio of starch:Eudragit® S of 50:50. The mixture was mixed for 2 h, 20% triethyl citrate (based on total polymer weight) and 5% glyceryl monostearate (GMS, based on total polymer weight) were added and mixing continued for a further 2 h.

13.18% iron oxide red (based on Eudragit® polymer weight) and 2.27% iron oxide yellow (based on Eudragit® polymer weight) were suspended in ethanol under high shear homogenization and this suspension was added into the starch and Eudragit mixture and mixing continued for a further 30 minutes.

The GMS was added in the form of an emulsion prepared at a concentration of 5% w/w. Polysorbate 80 (40% based on GMS weight) was dissolved in distilled water followed by dispersion of the GMS. This dispersion was then heated to 75° C. for 15 minutes under strong magnetic stirring in order to form an emulsion. The emulsion was cooled to room temperature under stirring. The final preparation was coated onto the inner layer coated tablets using a perforated pan coater until a coating having 5 mg Eudragit® S polymer/cm² was obtained. The spray coating parameters were as follows: spraying rate 8.0 g/min/kg tablets, atomizing pressure 0.4 bar, inlet air volume 100 m³/h/kg tablets and product temperature 35.5° C.

Comparative Example 1

(400 mg 5ASA tablets with inner layer of neutralised Eudragit® S/outer layer of Eudragit® S)

Inner Layer

The inner layer was prepared according to Example 1.

Outer Layer

The outer layer was prepared according to Example 1

Comparative Example 2

(400 mg 5ASA tablets with a single layer of Eudragit® S)

The single layer of Eudragit S was prepared according to Example 1 and applied directly on 400 mg 5ASA tablet cores (without isolation and without inner layer).

Comparative Example 3

(800 mg 5ASA tablets with inner layer of neutralised Eudragit® S/outer layer of a 30:70 mixture of starch:Eudragit® S)

Inner Layer

The inner layer was prepared according to Example 2.

Outer Layer

The outer layer was prepared according to Example 2.

Comparative Example 4

(800 mg 5ASA tablets with isolation layer of HPMC/outer layer of a 30:70 mixture of starch:Eudragit® S)

Isolation Layer

The isolation layer was prepared according to Example 2

Outer Layer

The outer layer was prepared according to Example 2

Comparative Example 5

(800 mg 5ASA tablets with a single layer of a 30:70 mixture of starch/Eudragit® S)

The single layer of a 30:70 mixture of starch/Eudragit® S was prepared according to Example 2, and applied directly on 800 mg 5ASA tablet cores (without isolation layer and without inner layer).

Comparative Example 6

(1200 mg 5ASA tablets with isolation layer of HPMC (1 mg/cm$^2$)/inner layer of neutralised Eudragit® S/outer layer of 30:70 mixture of starch:Eudragit® S)
Isolation Layer The isolation layer was applied from a mixture of HPMC and 20% polyethylene glycol 6000 (PEG 6000), based on dry polymer weight.

The HPMC polymer was dissolved in water under magnetic stirring and then PEG 6000 was added. The final preparation was sprayed onto 1200 mg 5-ASA cores using a perforated pan-coating machine to achieve a coating amount of 1 mg polymer/cm$^2$ to form isolation layer coated tablets.

The coating parameters were as follows: spray rate 9.75 g/min. per kg tablet cores, atomizing pressure 0.7 bar, inlet air volume 75 m$^3$/h/kg tablets and product temperature 32° C.
Inner Layer The inner layer was prepared according to Example 4
Outer Layer The outer layer was prepared according to Example 4.

Comparative Example 7

(1200 mg 5ASA tablets with isolation layer of HPMC (5 mg/cm$^2$)/inner layer of neutralised Eudragit® S/outer layer of 30:70 mixture of starch:Eudragit® S)
Isolation Layer The isolation layer was formed from a mixture of HPMC and 20% polyethylene glycol 6000 (PEG 6000), based on dry polymer weight.

The HPMC polymer was dissolved in water under magnetic stirring and then PEG 6000 was added. The final preparation was sprayed onto 1200 mg 5ASA cores using a pan-coating machine to achieve a coating amount of 5 mg polymer/cm$^2$ to form isolation layer coated tablets.
Inner Layer The inner layer was prepared according to Example 4.
Outer Layer The outer layer was prepared according to Example 4.

Figure 1:
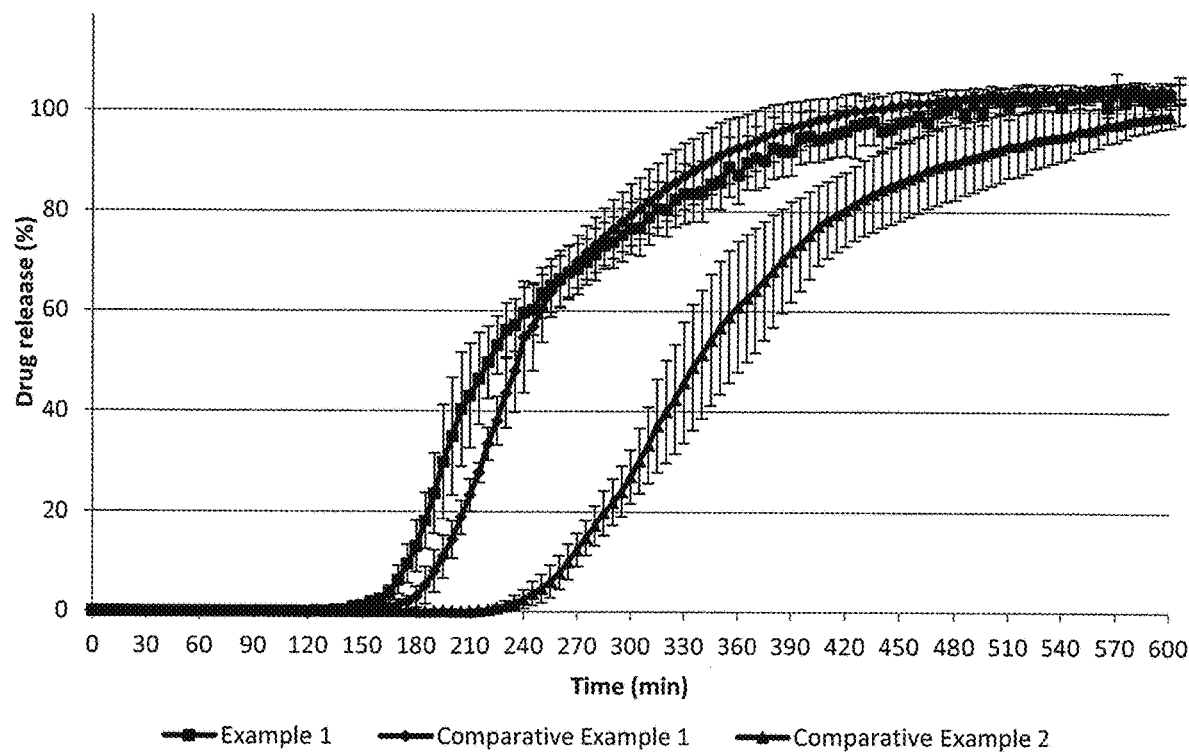

The coating parameters were as follows: spray rate 5.75 g/min. per kg tablet cores, atomizing pressure 0.7 bar, inlet air volume 75 m$^3$/h per kg tablet cores and product temperature 32° C.
Drug Release Test—Effect of pH Alone In vitro dissolution studies were performed on a USP type II apparatus using a paddle speed of 50 rpm and a media temperature of 37±0.5° C. Tablets were first tested in 0.1 M HCl for 2 h followed by 8 h in Krebs buffer (pH 7.4). The pH of the buffer was stabilized at 7.4±0.05 by continuously sparring with 5% $CO_2$/95% $O_2$. Absorbance measurements were taken at 5 minute intervals, with an absorbance wavelength of 301 nm in HCl and 330 nm in Krebs buffer. The composition per litre of Krebs buffer is 0.16 g of $KH_2PO_4$, 6.9 g of NaCl, 0.35 g KCl, 0.29 g $MgSO_4.7H_2O$, 0.376 g $CaCl_2.2H_2O$ and 2.1 g $NaHCO_3$. Only the measurements taken at 30 or 60 minute intervals are depicted in the figures.
Storage Drug release was tested before storage (Initial) and after storage under different conditions at the 1 month and 3 month points. The storage conditions exemplified herein are (i) open HDPE bottles at 25° C./60% RH (relative humidity); (ii) closed HDPE bottles at 25° C./60% RH; (iii) open HDPE bottle at 40° C./75% RH; and (iv) closed HDPE bottles 40° C./75% RH.
Results The results depicted in FIG. 1 clearly indicate that initial drug release is quicker (i.e. $T_{lag}$ is reduced) from 400 mg 5ASA tablets coated with an isolation layer of HPMC, an inner layer of neutralized Eudragit S and an outer layer of Eudragit S (Example 1) than if the isolation layer is absent (Comparative Example 1) or both the isolation layer and the inner layer are absent (Comparative Example 2).

Figure 2:
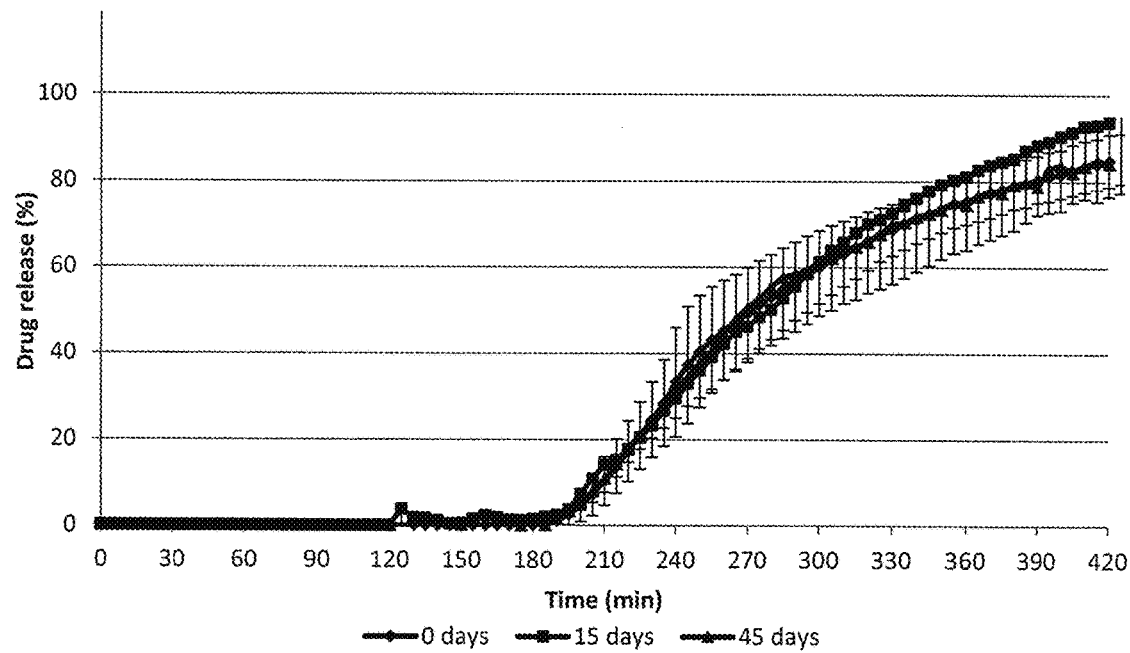
FIG. 2 is a graph comparing drug release in 0.1N HCl (2 h) followed by Krebs buffer pH 7.4 as a function of time from 400 mg 5ASA tablets coated with an isolation layer of HPMC, an inner layer of neutralized Eudragit® S and an outer layer of Eudragit® S (Example 1) after storage at 40° C./75% RH for (a) 0 days, (b) 15 days and (c) 45 days.
Figure 3:
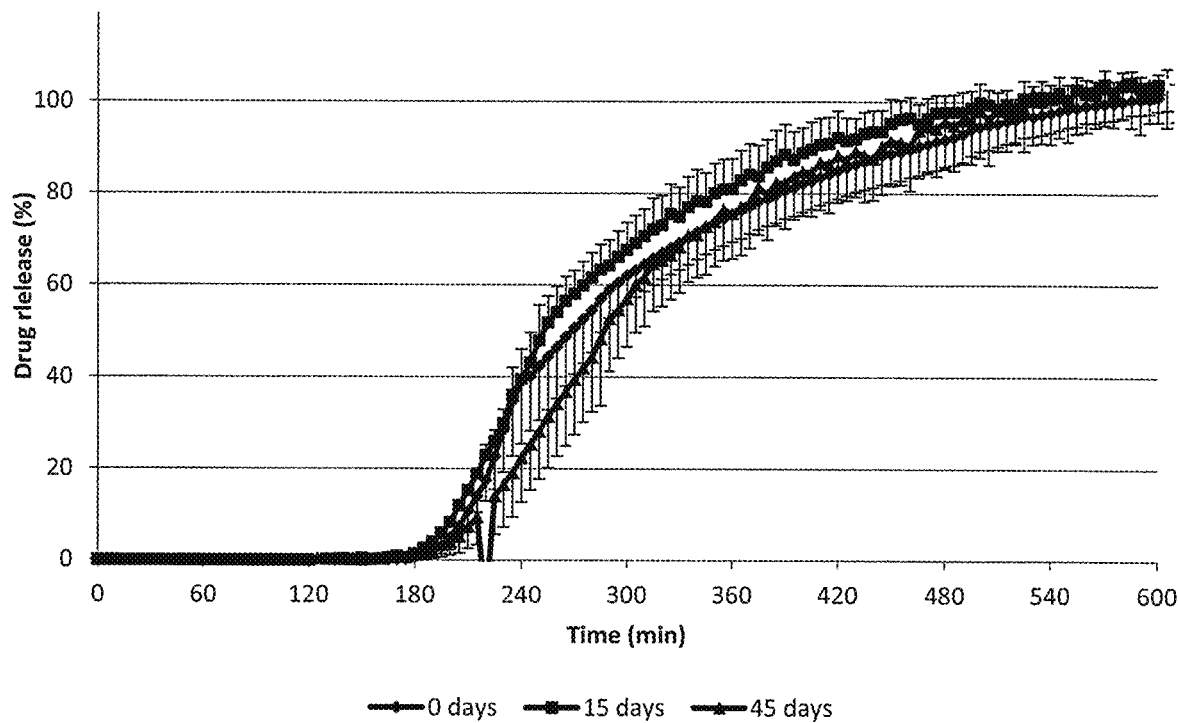
FIG. 3 is a graph comparing drug release in 0.1N HCl (2 h) followed by Krebs buffer pH 7.4 as a function of time from 400 mg 5ASA tablets coated with an inner layer of neutralized Eudragit® S and an outer layer of Eudragit® S (Comparative Example 1) after storage at 40° C./75% RH for (a) 0 days, (b) 15 days and (c) 45 days.

The results depicted in FIGS. 2 to 3 indicate that the drug release is substantially unaffected after storage (at 40° C./75% RH) after 45 days from tablets coated with an HPMC isolation layer, an inner layer of neutralized Eudragit S and outer layer of Eudragit S (Example 1) when compared to equivalent tablets without the isolation layer (Comparative Example 1). Clearly, the use of an HPMC isolation layer improves the stability of the tablets during storage.

The results depicted in FIG. 5 indicate that initial release drug release is quicker from 1200 mg 5ASA tablets coated with an isolation layer of HPMC, an inner layer of neutralized Eudragit S and an outer layer of a 30:70 mixture of starch:Eudragit S when the isolation layer has a thickness of 3 mg polymer/cm$^2$ (Example 4) than if the isolation layer has a thickness of 1 mg polymer/cm$^2$ (Comparative Example 6) or 5 mg polymer/cm$^2$ (Comparative Example 7)) although it should be noted that initial release is accelerated in each of these cases.

Turning to FIGS. 4 to 11, the results indicate that presence of an isolation layer made of HPMC (Example 2) leads to a faster drug release compared to tablets coated only with an inner layer of neutralized Eudragit S and an outer layer of a 30:70 mixture of starch:Eudragit S (Comparative Example 3). Furthermore, in the absence of the middle layer (Comparative Example 4), the isolation layer contributes to a later drug release when compared to a single layer of 30:70 mixture of starch:Eudragit S (Comparative Example 5). This result demonstrates that improved drug release is not inevitable if an isolation layer is present between the core and the alkaline inner layer.

Moreover, when using an isolation layer of PVA, the contribution to drug release acceleration was actually higher than the one given by the inner layer alone (Example 3, Comparative Example 3 and Comparative Example 9). In the absence of isolation layer (Comparative Example 3), after 1 month storage at 40° C./75% RH, the drug release was delayed even if stored in closed HDPE bottles. However, the presence of an HPMC isolation layer (Example 2) avoided the delay in drug release after 1 month at 40° C./75% RH for the tablets stored in closed HDPE bottles. The same observations are also valid when the outer layer has a 50:50 mixture of starch and Eudragit S (Example 5).

At 25° C./60% RH, even in open conditions, there is no significant change in drug release if an isolation layer is present (Example 2 and Example 5), whereas in the absence of the isolation layer (Comparative Example 3), tablets stored openly show a delayed release after 1 month.

It can be seen therefore that the delayed release formulation according to the present invention is significantly superior to comparative formulations.

Whilst the invention has been described with reference to a preferred embodiment, it will be appreciated that various modifications are possible within the spirit or scope of the invention as defined in the following claims.

In this specification, unless expressly otherwise indicated, the word 'or' is used in the sense of an operator that returns a true value when either or both of the stated conditions is met, as opposed to the operator 'exclusive or' which requires that only one of the conditions is met. The word 'comprising' is used in the sense of 'including' rather than in to mean 'consisting of'. All prior teachings acknowledged above are hereby incorporated by reference. No acknowledgement of any prior published document herein should be taken to be an admission or representation that the teaching thereof was common general knowledge in Australia or elsewhere at the date hereof.

The invention claimed is:

1. A dosage form, comprising:
   a delayed release drug formulation for oral administration to a subject in need thereof, said formulation comprising:
   a core comprising said drug;
   an isolation layer comprising at least one non-ionic polymer, said isolation layer coating said core; and
   an outer coating for providing intestinal release of said drug, said outer coating comprising an outer layer and an inner layer,
   wherein said outer layer comprises a pH dependently soluble polymeric material which has a pH threshold at about pH 5 or above,
   wherein the inner layer comprises (i) a soluble polymeric material which is a non-ionic polymer soluble in intestinal fluid or gastrointestinal fluid selected from the group consisting of methylcellulose (MC); hydroxypropyl cellulose (HPC); hydroxypropyl methylcellulose (HPMC); poly(ethylene oxide)-graft-polyvinyl alcohol; polyvinylpyrrolidone (PVP); and polyvinyl alcohol (PVA), (ii) a base wherein said base is a hydroxide base, and (iii) a buffer agent wherein said buffer agent is a phosphate salt and is present in the inner layer in a total amount from about 10 wt % to about 30 wt % based on a dry weight of the soluble polymeric material which is the non-ionic polymer of the inner layer,
   wherein the inner layer is disposed between the isolation layer and the outer layer, and
   wherein a composition of the isolation layer and a composition of the inner layer are different.

2. The dosage form of claim 1, wherein intestinal release of said drug from said delayed release drug formulation is accelerated compared to an equivalent formulation without said isolation layer.

3. The dosage form of claim 1, for use in accelerating drug release in the colon of said subject.

4. The dosage form of claim 3, wherein lag time ($T_{lag}$) in vitro in Krebs buffer at pH 7.4 after 2 h at 0.1M HCl is reduced by at least 10 %.

5. The dosage form of claim 3, wherein lag time ($T_{lag}$) in vitro in Krebs buffer at pH 7.4 after 2 h at 0.1M HCl is reduced by at least 10 minutes.

6. The dosage form of claim 1, for use in accelerating drug release in the small intestine of said subject.

7. The dosage form of claim 1, for use in accelerating drug release in the proximal small intestine of said subject.

8. The dosage form of claim 1, wherein the isolation layer has a coating amount from about 1 mg polymer/cm$^2$ to about 5 mg polymer/cm$^2$.

9. The dosage form of claim 1, wherein the isolation layer has a thickness from about 5 µm to about 100 µm.

10. The dosage form of claim 1, wherein said at least one non-ionic polymer of the isolation layer is selected from the group consisting of methylcellulose (MC); hydroxypropyl cellulose (HPC); hydroxypropyl methylcellulose (HPMC); poly(ethylene oxide)-graft-polyvinyl alcohol; polyvinylpyrrolidone (PVP); and polyvinyl alcohol (PVA).

11. The dosage form of claim 1, wherein said at least one non-ionic polymer of the isolation layer is hydroxypropyl methylcellulose (HPMC).

12. The dosage form of claim 1, wherein said at least one non-ionic polymer of the isolation layer is polyvinyl alcohol (PVA).

13. The dosage form of claim 1, wherein said at least one non-ionic polymer of the isolation layer is the only film-forming polymeric material in the isolation layer.

14. A dosage form, comprising:
   a delayed release drug formulation for oral administration to deliver a drug to the intestine of a subject in need thereof, said formulation comprising:
   a core comprising said drug;
   an isolation layer comprising a non-ionic polymer, said isolation layer coating said core, said isolation layer for use in accelerating drug release in the intestine of said subject; and
   an outer coating for providing intestinal release of said drug, said outer coating comprising an outer layer and an inner layer,
   wherein the outer layer comprises a film-forming polymeric material consisting of a pH dependently soluble polymeric material which has a pH threshold at about pH 5 or above,
   wherein the inner layer comprises (i) a soluble polymeric material which is a non-ionic polymer soluble in intestinal fluid or gastrointestinal fluid, (ii) a base wherein said base is a hydroxide base, and (iii) a buffer agent wherein said buffer agent is a phosphate salt and is present in the inner layer in a total amount from about 10 wt % to about 30 wt % based on a dry weight of the soluble polymeric material which is the non-ionic polymer of the inner layer,
   wherein the inner layer is disposed between the isolation layer and the outer layer, and
   wherein a composition of the isolation layer and a composition of the inner layer are different.

15. The dosage form of claim 14, wherein said core is acidic.

16. The dosage form of claim 14, wherein said drug, or any other component in the core, comprises at least one acidic group.

17. The dosage form of claim 14, wherein said drug is an anti-inflammatory agent.

18. The dosage form of claim 14, wherein said drug is 5ASA.

19. The dosage form of claim 14, wherein the buffer agent is potassium dihydrogen phosphate.

20. The dosage form of claim 14, wherein the base is sodium hydroxide.

21. The dosage form of claim 14, wherein the pH dependently soluble polymeric material of the outer layer is a blend of at least two different polymers having a pH threshold of about pH 5 and above.

22. The dosage form of claim 21, wherein the polymers in the blend are different polymethacrylate polymers.

23. The dosage form of claim 21, wherein there are two different polymers in the blend in a ratio from about 40:60 to about 60:40.

24. The dosage form of claim 14, wherein said pH dependently soluble polymeric material is present in the outer layer as the sole film forming polymeric material.

25. The dosage form of claim 14, wherein said pH dependently soluble polymeric material is present in the outer layer in admixture with a digestible polymeric material which is susceptible to attack by colonic bacteria.

26. The dosage form of claim 25, wherein said digestible polymeric material and said pH dependently soluble polymeric material are present in the outer layer in a ratio of up to about 60:40.

27. The dosage form of claim 25, wherein said digestible polymeric material and said pH dependently soluble polymeric material are present in the outer layer in a ratio from about 25:75 to about 35:65.

28. The dosage form of claim 25, wherein said digestible polymeric material and said pH dependently soluble polymeric material are present in the outer layer in a ratio from about 40:60 to about 60:40.

29. The dosage form of claim 14, wherein release of said drug in the intestine is accelerated.

30. A method, comprising:
accelerating drug release in an intestine of a subject in need thereof by administering to the subject a delayed release drug formulation, said formulation comprising:
a core comprising said drug;
an isolation layer comprising a non-ionic polymer, said isolation layer coating said core; and
an outer coating for providing intestinal release of said drug, said outer coating comprising an outer layer and an inner layer,
wherein the outer layer comprises a pH dependently soluble polymeric material which has a pH threshold at about pH 5 or above,
wherein the inner layer comprises (i) a soluble polymeric material which is a non-ionic polymer soluble in intestinal fluid or gastrointestinal fluid selected from the group consisting of methylcellulose (MC); hydroxypropyl cellulose (HPC); hydroxypropyl methylcellulose (HPMC); poly(ethylene oxide)-graft-polyvinyl alcohol; polyvinylpyrrolidone (PVP); and polyvinyl alcohol (PVA), (ii) a base, and (iii) a buffer agent, wherein said buffer agent is a phosphate salt and is present in the inner layer in a total amount from about 10 wt % to about 30 wt % based on a dry weight of the soluble polymeric material which is the non-ionic polymer of the inner layer,
wherein the inner layer is disposed between the isolation layer and the outer layer, and
wherein a composition of the isolation layer and a composition of the inner layer are different.

31. A method of producing a delayed release drug formulation for oral administration, comprising:
obtaining a core comprising said drug;
coating said core with an isolation layer to produce an isolated core, the isolation layer comprising a non-ionic polymer; and
coating said isolated core with an outer coating for providing intestinal release of said drug, said outer coating comprising an outer layer and an inner layer,
wherein the outer layer comprises a pH dependently soluble polymeric material which has a pH threshold at about pH 5 or above,
wherein the inner layer comprises (i) a soluble polymeric material which is a non-ionic polymer soluble in intestinal fluid or gastrointestinal fluid selected from the group consisting of methylcellulose (MC); hydroxypropyl cellulose (HPC); hydroxypropyl methylcellulose (HPMC); poly(ethylene oxide)-graft-polyvinyl alcohol; polyvinylpyrrolidone (PVP); and polyvinyl alcohol (PVA), (ii) a base, and (iii) a buffer agent, wherein said buffer agent is a phosphate salt and is present in the inner layer in a total amount from about 10 wt % to about 30 wt % based on a dry weight of the soluble polymeric material which is the non-ionic polymer of the inner layer,
wherein the inner layer is disposed between the isolation layer and the outer layer, and
wherein a composition of the isolation layer and a composition of the inner layer are different,
wherein said formulation provides accelerated release of a drug in an intestine of a subject in need thereof.

\* \* \* \* \*

UNITED STATES PATENT AND TRADEMARK OFFICE
CERTIFICATE OF CORRECTION

PATENT NO. : 11,517,534 B2
APPLICATION NO. : 15/612065
DATED : December 6, 2022
INVENTOR(S) : Felipe José Oliveira Varum et al.

It is certified that error appears in the above-identified patent and that said Letters Patent is hereby corrected as shown below:

On the Title Page

Column 2, Line 9, U.S. 5,914,132 in item (56) U.S. PATENT DOCUMENTS currently reads: "Keim"

And should read:
--Kelm--;

Page 2, Column 1, Line 8, in item (56) FOREIGN PATENT DOCUMENTS currently reads: "2008-21429"

And should read:
--2008-214249--;

Page 2, Column 2, Line 43, in item (56) OTHER PUBLICATIONS currently reads: "1999;"

And should read:
--1999,--;

Page 2, Column 2, Line 51, in item (56) OTHER PUBLICATIONS currently reads: "McCconnell"

And should read:
--McConnell--;

Page 2, Column 2, Line 61, in item (56) OTHER PUBLICATIONS currently reads: "Rowem"

Signed and Sealed this
Second Day of May, 2023

Katherine Kelly Vidal
*Director of the United States Patent and Trademark Office*

And should read:
--Rowe,--;

Page 2, Column 2, Line 63, in item (56) OTHER PUBLICATIONS currently reads: "Hanbook"

And should read:
--Handbook--;

Page 2, Column 2, Line 66, in item (56) OTHER PUBLICATIONS currently reads: "Hanbook"

And should read:
--Handbook--; and

Page 3, Column 1, Line 2, in item (56) OTHER PUBLICATIONS currently reads: "Slan"

And should read:
--Sian--.